United States Patent [19]
Ohtomo

[11] Patent Number: 5,895,357
[45] Date of Patent: Apr. 20, 1999

[54] BONE ASSESSMENT APPARATUS

[75] Inventor: Naoki Ohtomo, Mitaka, Japan

[73] Assignee: Aloka Co., Ltd., Mitaka, Japan

[21] Appl. No.: 08/789,631

[22] Filed: Jan. 27, 1997

[30] Foreign Application Priority Data

| Jan. 29, 1996 | [JP] | Japan | 8-012700 |
| Jan. 29, 1996 | [JP] | Japan | 8-012995 |
| Jan. 30, 1996 | [JP] | Japan | 8-013477 |
| Feb. 2, 1996 | [JP] | Japan | 8-017327 |

[51] Int. Cl.$^6$ ..................... A61B 3/00
[52] U.S. Cl. ..................... 600/449; 600/459
[58] Field of Search ............. 600/437, 442, 600/445, 449, 459; 73/597, 599

[56] References Cited

U.S. PATENT DOCUMENTS

| 3,847,141 | 11/1974 | Hoop . | |
| 4,275,597 | 6/1981 | Quedens et al. | 600/445 |
| 4,603,701 | 8/1986 | Chen | 600/459 |
| 5,134,999 | 8/1992 | Osipor | 600/449 |
| 5,335,661 | 8/1994 | Koblonshi | 600/449 |
| 5,348,009 | 9/1994 | Ohtomo et al. . | |

FOREIGN PATENT DOCUMENTS

| 0 004 845 | 10/1979 | European Pat. Off. . |
| 0 576 217 A1 | 12/1993 | European Pat. Off. . |
| 0 730 364 3 | 11/1995 | European Pat. Off. . |
| 0 719 520 A2 | 7/1996 | European Pat. Off. . |
| 0 737 440 A1 | 10/1996 | European Pat. Off. . |
| 6-254099 | 9/1994 | Japan . |
| 6-327669 | 11/1994 | Japan . |
| 7-204205 | 8/1995 | Japan . |
| 7-303643 | 11/1995 | Japan . |

*Primary Examiner*—Francis J. Jaworski
*Attorney, Agent, or Firm*—Fishman, Dionne, Cantor & Colburn

[57] ABSTRACT

A bone assessment apparatus for diagnosing bone by transmitting and receiving measuring waves (in particular ultrasonic waves) is provided. A body part (e.g. a foot) is gripped by a pair of transducer assemblies, and ultrasonic waves are transmitted and received in this state. Each transducer assembly comprises an ultrasonic transducer and a coupler. The transverse cross-sectional area of the ultrasonic wave beam is adjusted by adjusting the contact area of the coupler on the body part, by changing the vibrating area of the ultrasonic transducer, or by fitting an attachment which narrows the ultrasonic wave beam to the transducer assembly. The transverse cross-sectional area of the ultrasonic wave beam may be changed depending on the size of the body part to be measured.

19 Claims, 19 Drawing Sheets

BONE ASSESSMENT APPARATUS

BACKGROUND OF THE INVENTION

1. Field of the Invention

This invention relates to a bone assessment apparatus, and more particularly to an apparatus which uses ultrasonic waves to assess bone.

2. Description of the Prior Art

Many types of apparatus have so far been proposed to assess bone by using ultrasonic waves (ultrasound). For example, in a bone assessment apparatus disclosed by U.S. Pat. No. 3,847,141, the heel of the foot is enclosed between a pair of ultrasonic transducers, and the bone is assessed by passing ultrasonic waves through the heel.

In this conventional apparatus, soft rubber pads are provided on the front of each transducer. When there is an air layer having a considerably different acoustic impedance in the propagation path of the ultrasonic waves, the ultrasonic waves are attenuated and reflected by the air layer. The above rubber pads solve this problem.

Another type of bone assessment apparatus is disclosed by Tokkai (Japanese Patent Laid-Open) Hei 6-22960 (U.S. Pat. No. 5,348,009) and Tokkai Hei 6-254099. In this type of bone assessment apparatus, a pair of ultrasonic transducers are disposed a fixed distance apart in a tank filled with a coupling liquid, however it has been pointed out that handling of the tank is difficult.

Another type of bone assessment apparatus which does not use a tank is disclosed in Tokkai Hei 7-204205. In this conventional apparatus, each one of a pair of transducer assemblies equipped with ultrasonic transducers is disposed on either side of a body part, and a fluid bag containing a coupling liquid is disposed in front of the ultrasonic transducers. This fluid bag is relatively large. The surface of the bag in contact with the body part is rectangular, and it is slightly inflated on the outside (side in contact with the body part). The bag is capable of overall deformation, however the area of contact with the body part does not change even when the bag deforms. According to this conventional apparatus, the bag and coupling liquid are always interposed between the transducers and surface of the body part.

A similar type of bone assessment apparatus is disclosed in Tokkai Hei 7-303643. According to this apparatus, a pressure sensor which detects the pressure of the transducer assembly on the body part is provided inside the fluid bag. In this way, ultrasonic waves can be sent and received while maintaining a constant pressure.

However in all of the above bone assessment apparatuses, it was impossible to vary the cross-sectional area of the ultrasonic beam emitted toward the body part (i.e. the spot area of the ultrasonic beam on the bone surface). In other words, in the prior art, the width of the ultrasonic beam was not controlled.

The bone assessment apparatus commonly found today is used for diagnosing relatively elderly people who are more susceptible to bone diseases such as osteoporosis. Hence, the cross-sectional area of the ultrasonic beam was set to correspond with the bone of an adult (e.g. calcaneous or heel bone).

Notwithstanding this, in recent years, there is an increasing need to assess the bones of younger persons (children) to prevent and diagnose bone disease. Prevention and early treatment require early bone diagnosis.

However the conventional bone assessment apparatus was set to perform measurements on adults as described above, and when it was used to assess children's bones, the following problems arose. These problems will now be described with reference to FIG. 1.

FIG. 1 shows an adult's foot (near the heel). 10 is a calcaneous or heel, 12 is a talus or ankle bone, 14 is a navicular bone, and 16 is a cuboid bone. As the calcaneous 10 comprises a large amount of trabecula bone, structural changes due to bone diseases such as osteoporosis tend to appear often in it, so it is common to diagnose the calcaneous 10 when assessing the bone. Conventionally, a spot 18 (i.e. the irradiating surface area of the ultrasonic beam on the calcaneous) was set to the size of a normal adult's calcaneous as shown in FIG. 1.

However, if the diameter of the spot is not changed and the ultrasonic beam is transmitted to the calcaneous 10 of a child as shown in FIG. 2, a first problem is that the spot 18 of the beam overlaps the calcaneous 10 as shown by the symbol 20. Secondly, another problem is that the ultrasonic beam is transmitted to a join 22 of the bones.

When the first problem occurs, although the object is to perform measurements on the bone, data is obtained also for areas that do not comprise bone, and this adversely affects the reliability of the measurements. Regarding the second problem, the joint between the bones is structurally unique (e.g. the speed of sound is extremely high in that area), so the reliability of bone assessment again falls when the bone is assessed using the speed of sound.

These problems are not limited to ultrasonic measurements on children, and occur also when such measurements are made on adults who have small foot bones.

Another problem was that in the prior art, the measurement point could not be suitably and automatically positioned.

In the bone assessment apparatus disclosed in the aforesaid U.S. Pat. No. 3,847,141, no mechanism to adjust the measurement point was provided, and it was extremely difficult to set this point appropriately according to the size of the subject's foot.

In the aforesaid Tokkai Hei 6-22960, a scanning mechanism is disclosed to position and adjust the measurement point. In this disclosure, the measurement point of the ultrasonic beam is determined based on a two-dimensional X-ray image, but this determination is made by the operator.

In Tokkai Hei 6-327669, a device is proposed for automatically determining the measurement point from an outline image of the bone, however in order to obtain such an outline image, it is necessary for example to scan the bone in two dimensions by an X ray beam.

In the aforesaid Tokkai Hei 7-204205, a mechanism is disclosed to position the measurement point, however no provision is made to control this positioning in accordance with the size of the subject's body part (e.g. foot).

Consequently, in the prior art it was either impossible to adjust the measurement point to suit the size of the body part to be measured, or the adjustment could not be performed without a complex mechanism or an arbitrary human decision.

Bone assessments are performed on many different people, some of whom have large body part (e.g. foot) and of whom others have small body part. Moreover, bone assessments have to be performed not only on adults but also on children. In such cases, when a bone assessment is performed without considering the size of the body part being assessed, the measuring wave (ultrasonic beam or X-ray) may not reach the center of the body part and unexpected reflections or scattering may occur so that the reliability of the results obtained declines.

SUMMARY OF THE INVENTION

It is therefore an object of this invention, which was conceived in view of the aforesaid problems, to provide a bone assessment apparatus which can perform highly precise measurements in accordance with the size of a body part to be measured.

It is another object of this invention to provide a bone assessment apparatus wherein the spot area of an ultrasonic beam may be varied in accordance with the size of the body part to be measured to improve the reliability of the bone assessment results obtained.

It is a further object of this invention to provide a bone assessment apparatus wherein the area of the measuring beam may be adjusted by a simple mechanism.

It is a further object of this invention to provide a bone assessment apparatus wherein the spot area of the measuring beam may be adjusted by a simple user operation.

It is a still further object of this invention to provide a bone assessment apparatus wherein the measurement point may be automatically and rapidly positioned.

(1) In order to achieve the above objectives, the bone assessment apparatus according to this invention comprises:
  at least one transducer assembly comprising an ultrasonic transducer, and
  adjusting means to adjust the area of an ultrasonic beam cross-section formed by this transducer assembly.

(2) In order to achieve the above objectives, the bone assessment apparatus according to this invention comprises:
  at least one transducer assembly comprising an ultrasonic transducer and a coupler provided in front of the assembly,
  an assembly drive mechanism to displace the transducer assembly so that the coupler comes in contact with a body part, and
  adjusting means to adjust the area of the coupler in contact with the body part by controlling the assembly drive mechanism
  wherein the adjusting means adjusts the area of an ultrasonic beam aperture by adjusting the contact area of the coupler.

According to the above construction, a coupler (or coupling dome) is provided in front of the transducer in the transducer assembly (transducer unit). When the assembly is moved toward the body, the bulge of the coupler first comes in contact with the body. When the assembly is moved further in the same direction, the pressure on the body part increases, and the deformation (crushing amount) of the coupler increases so that the area in contact with the body gradually enlarges. The area of the coupler in contact with the body actually corresponds to the ultrasonic beam aperture, hence the cross-sectional area of the beam (i.e. the cross-sectional area perpendicular to the beam axis) may be changed by varying the contact area of the coupler.

In other words, the size of the beam spot can be adjusted by a simple construction without performing any special control of the transmitted or received signals.

Preferably, the coupler comprises a membrane capable of elastic deformation and a coupling liquid which fills the interior of this membrane, and this coupler has a dome-like shape of which the area in contact with the body changes depending on the magnitude of the pressure of the coupler on the body.

In a preferred form of the invention, the contact area of the coupler varies from a minimum area to a maximum area depending on the magnitude of its pressure on the body, the maximum area being equal to or greater than the area of the vibrating surface of the ultrasonic transducer.

In a preferred form of the invention, the adjusting means mentioned above comprises a pressure detecting means for detecting the pressure of the coupler on the body part, and a stop control means which stops the transducer assembly from being driven when this pressure reaches a limiting value selected from a plurality of limiting values.

(3) In order to achieve the above objectives, the bone assessment apparatus according to this invention comprises:
  at least one transducer comprising an ultrasonic transducer of which the vibrating area can be changed, and a coupler which propagates ultrasonic waves between this ultrasonic transducer and a body part, and
  adjusting means for adjusting the size of the cross-section of the ultrasonic wave beam by changing the vibrating area.

According to the aforesaid construction, the adjusting means changes the vibrating area in the ultrasonic transducer according to the size of body part to be measured. Therefore by suitably setting the vibrating area, measurements can be performed using an ultrasonic beam having a suitable width for the size of body part to be measured.

(4) In order to achieve the above objectives, the bone assessment apparatus according to this invention comprises:
  at least one transducer assembly comprising an ultrasonic transducer, and
  at least one attachment which can be freely fitted to or removed from this transducer assembly, this attachment having an aperture for narrowing an ultrasonic beam,
  the size of the beam cross-section being adjusted by fitting this attachment to the ultrasonic assembly.

According to the aforesaid construction, when for example performing a bone assessment on small bones, the ultrasonic beam may be narrowed and its cross-sectional area reduced by fitting the attachment to the transducer assembly. The attachment may be fitted for example by the user, but the fitting may also be performed automatically. A plurality of attachments having apertures of different size may also be provided, and one of these selected according to the size of body part to be measured.

According to this preferred form of the invention, when the attachment is fitted to the transducer assembly, the coupler in the transducer assembly projects from the aperture, and the aperture is surrounded by a part (ring-shaped member) which absorbs ultrasonic waves and is capable of elastic deformation.

According to the aforesaid construction, when the transducer assembly to which the aperture adjusting attachment is fitted, is pressed onto the body part, the coupler elastically deforms, and the ring-shaped member of the aperture adjusting attachment elastically deforms. The ring-shaped member absorbs and blocks ultrasonic waves, and its internal aperture limits the width of the ultrasonic beam.

Further according to a preferred form of the invention, the invention comprises a fitting means to fit the attachment to the transducer assembly.

(5) In order to achieve the aforesaid objectives, the bone assessment apparatus according to this invention comprises:
  a measuring unit comprising a platform on which a body part is positioned,
  size determining means to measure the size of body part supported on the platform, and a measurement controller for determining the measuring conditions for assessing bone based on the size of body part.

Preferably, when the measuring unit transmits and receives ultrasonic waves, the measurement controller determines the measurement point of the ultrasonic beam according to the size of the body part to be measured.

According to the above construction, the size determining means determines the size of body part to be measured, and the measurement controller determines the measuring conditions, e.g. the beam transmitting/receiving measurement point, based on this measured size. According to this invention, therefore, a suitable measuring point can be automatically determined according to the size of body part to be measured, so measurement reproducibility and reliability are enhanced. This invention may of course be applied to a bone assessment apparatus having an adapter as a foot platform. In this case, for example in determining the measurement point, the adapter used may be automatically identified, and the measurement point determined taking account of its shape (thickness, etc.)

In a preferred form of this invention, the size measuring means comprises at least one of a first measuring means which measures the length of the planta of the foot from the edge of the heel to the tips of the toes, and a second measuring means which measures the height of the instep of the foot, and more preferably comprises both.

DESCRIPTION OF THE PREFERRED EMBODIMENTS

(1) Embodiments 1 and 2

Figure 3:
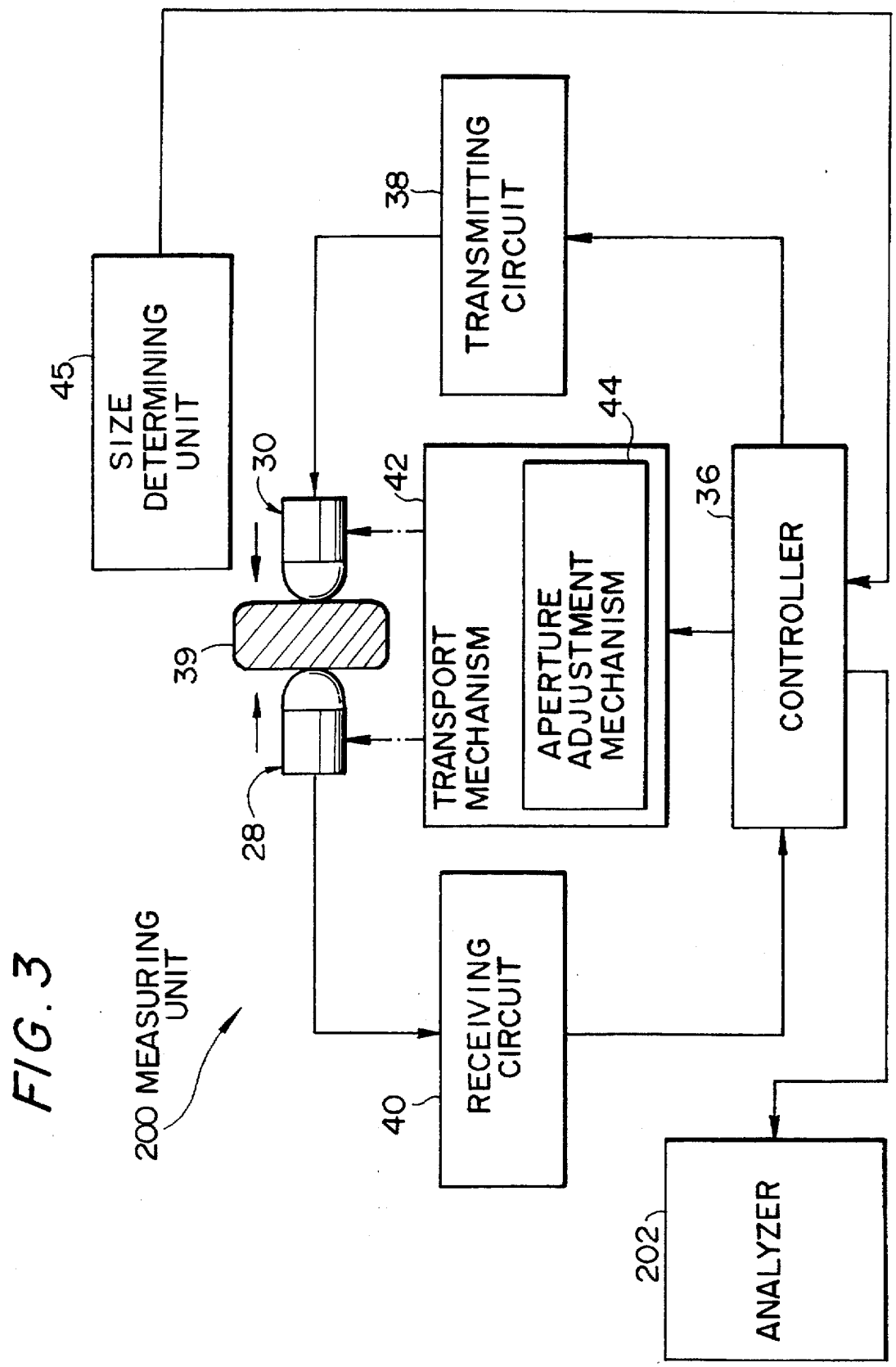
FIG. 3 is a diagram showing a first embodiment of an ultrasonic wave bone assessment apparatus according to this invention.

FIG. 3 shows the overall construction of a first embodiment of an ultrasonic wave bone assessment apparatus according to this invention.

This apparatus comprises a measuring unit 200 for performing measurements using ultrasonic waves, and an analyzer 202 for analyzing the results measured by the measuring unit, and computing bone diagnostic values therefrom. The analyzer 202 may for example be a computer.

Figure 4:
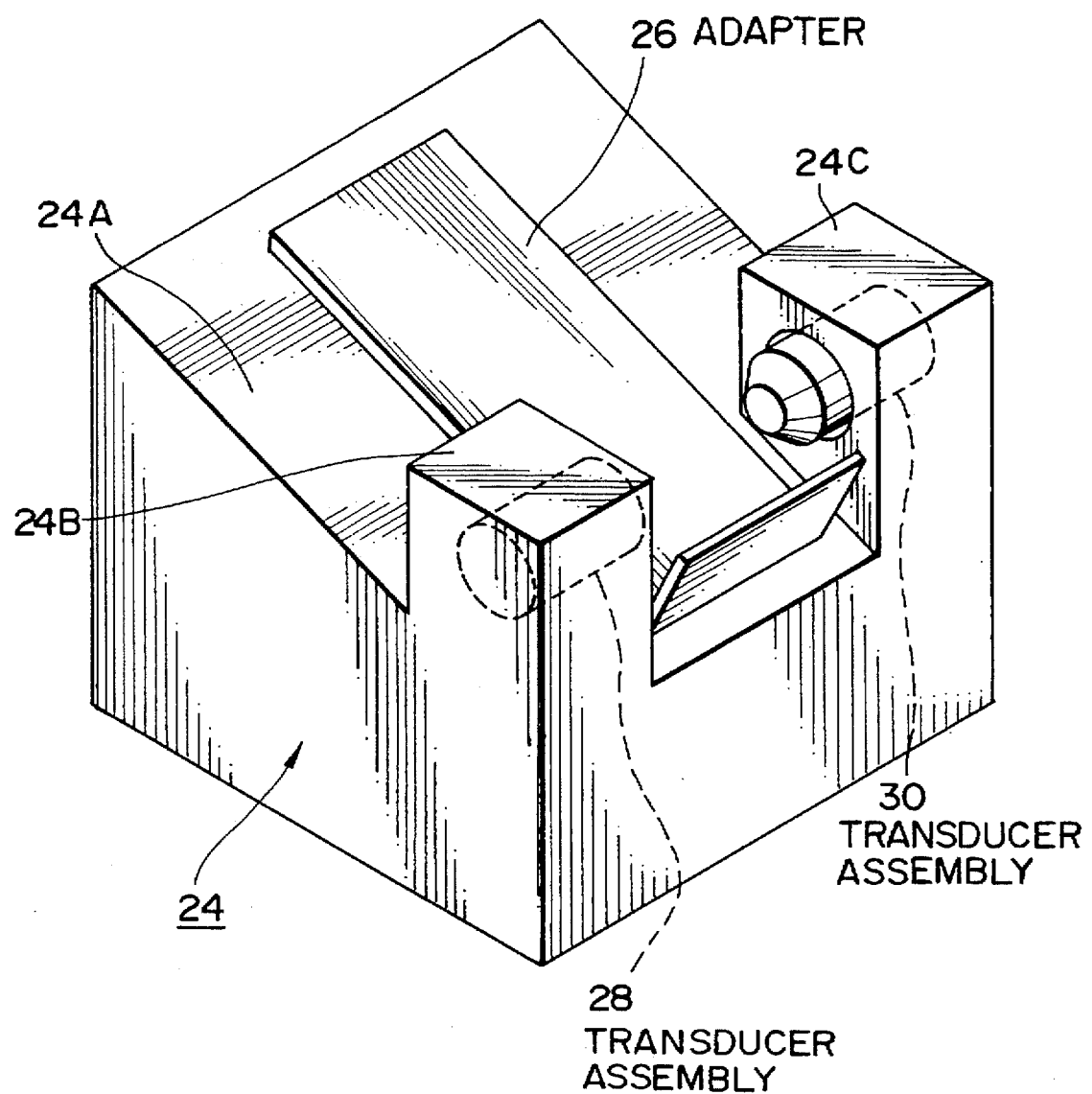
FIG. 4 is a diagram of the external appearance of an ultrasonic wave bone assessment apparatus according to this invention.

FIG. 4 shows the external appearance of the measuring unit 200. An upper surface 24A of a chassis 24 is slanted, and a foot platform (adapter) 26 is disposed on this upper surface 24A such that it may be freely interchanged as necessary. A plurality of foot platforms 26 of several types are provided for different foot sizes, one of these platforms 26 being selected for use. The thickness and shape, etc. of each foot platform 26 is different so that the center of the ultrasonic beam and the center of the calcaneous can be made to coincide by suitably choosing the platform 26.

Abutments 24B, 24C are formed on both sides of the foot platform 26 set on the upper surface 24A, and transducer assemblies 28, 30 are provided in the abutments 24B, 24C such that these assemblies are free to move forwards and backwards. The pair of transducer assemblies 28, 30 are driven by a drive mechanism (transport mechanism) described hereafter so that they may be made to approach each other or move apart. When a foot is placed on the platform 26 and the pair of transducer assemblies 28, 30 are made to approach each other, the heel of the foot is gripped from both sides by the pair of transducer assemblies 28, 30. When an ultrasonic beam is transmitted by one of the transducer assemblies in this state, an ultrasonic beam which has passed through the calcaneous is received by the other transducer assembly.

Figure 5:
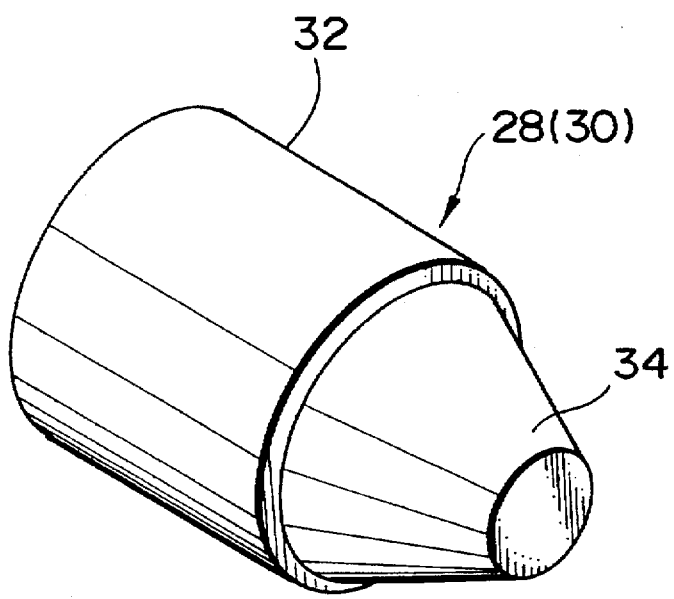
FIG. 5 is a diagram of the external appearance of a transducer assembly according to this invention.

FIG. 5 is a schematic diagram of the external appearance of the transducer assembly 28. Both of the transducer assemblies 28, 30 have an identical form and construction. According to this embodiment, the transducer assembly 28 comprises a chassis 32 housing a relatively large single ultrasonic transducer, and a conical coupler 34 (having a trapezoidal cross-section). The coupler 34 is disposed in vibration side of the transducer.

The coupler 34 is provided to improve ultrasonic wave propagation between the ultrasonic transducer and a body part.

The coupler 34 comprises a member capable of elastic deformation for achieving good contact with the body part, and for adjusting the cross-sectional area of the ultrasonic beam as described hereafter.

Figure 6:
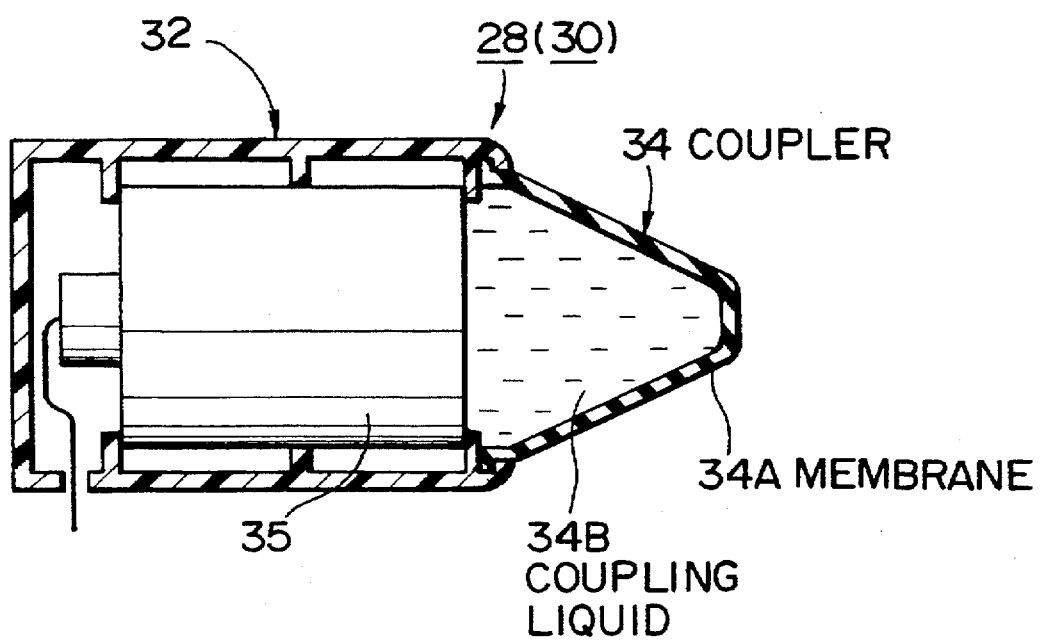
FIG. 6 is a view in section of a transducer assembly according to this invention.

According to this embodiment, the coupler 34 comprises a membrane 34A which defines its external contour, and a coupling liquid 34B (e.g. castor oil) which fills the interior of the membrane 34A as shown in FIG. 6. The coupler 34 deforms elastically according to the contact pressure on the body part. The transducer assembly 28 and body part are therefore in intimate contact, and according to this embodiment, the cross-sectional area of the ultrasonic beam path may be adjusted by adjusting the degree of elastic deformation.

Figure 7:
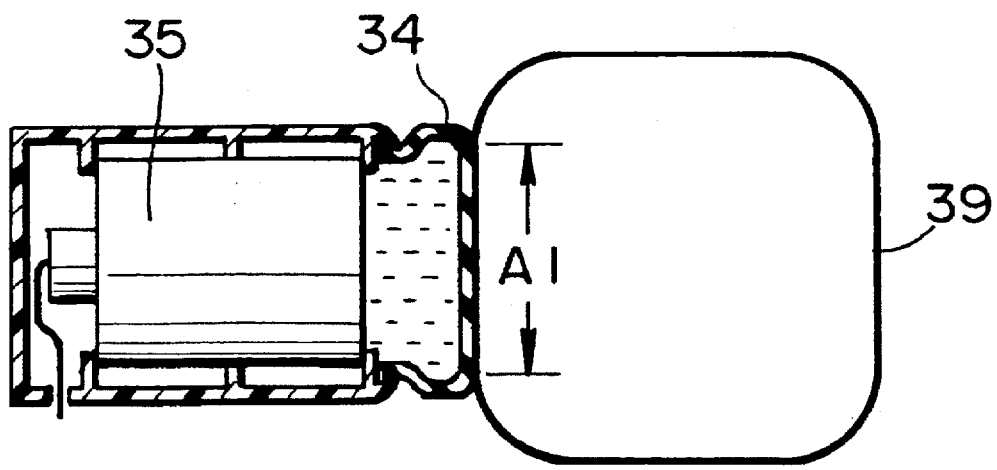
FIG. 7 is a diagram wherein a coupler is largely deformed so as to form a large ultrasonic beam aperture.
Figure 8:
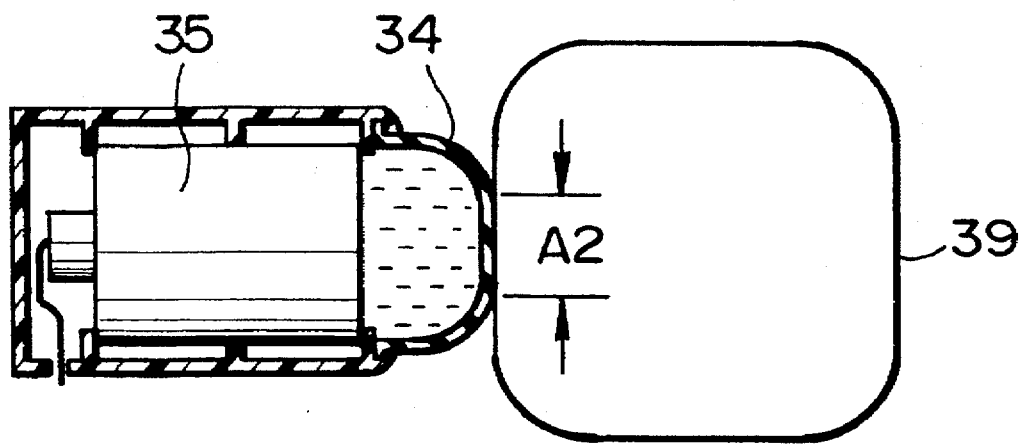
FIG. 8 is a diagram wherein a coupler is slightly deformed so as to form a small ultrasonic beam aperture.

FIG. 7 shows the state where the coupler 34 undergoes a large deformation by increasing the pressure of the transducer assembly on the body part. FIG. 8 shows the state where the coupler 34 undergoes a small deformation by decreasing the pressure of the transducer assembly on the body part. As shown in FIG. 7, by giving the coupler 34 a large deformation, a contact surface A1 between the coupler 34 and a body part 39 can be increased.

In this case, a the contact area A1 is set to be equal to or greater than the size of the front surface (vibrating surface) of the ultrasonic transducer 35.

On the other hand when the coupler 34 is given a small deformation so that a contact area A2 between the coupler 34 and body part 39 is reduced, the ultrasonic beam aperture can be narrowed, as shown in FIG. 8. In other words, the area of the contact surface effectively corresponds to the ultrasonic beam aperture, and by increasing or decreasing the area of the contact surface, the cross-sectional area of the ultrasonic beam (i.e. the irradiating area) can be increased or decreased.

According to this embodiment, the coupler 34 comprises a function for making acoustic adjustments (original function), and a function for adjusting the ultrasonic beam aperture (additional function). The shape of the coupler 34 must be such that the area of it which is in contact with the body part increases at least gradually with increase of pressure on the body part. For example, the coupler 34 is formed such that it becomes progressively narrower toward the front. Preferably, its profile is a cone of circular cross-section. When the coupler 34 is not deformed, its apical surface diameter may be for example 1 cm, its diameter on the transducer side may be for example 2.5 cm, and its length (height) may be for example 2-3 cm.

Returning to FIG. 3, a controller 36 controls measurements. Based on a trigger signal from the controller 36, a transmitting circuit 38 supplies a transmission drive signal to the transducer assembly 30. An ultrasonic wave (ultrasonic wave pulse) is thereby transmitted to a body part 39 from the transducer assembly 30.

When the ultrasonic wave passes through the body part 39, its characteristics change, and it is then received by the transducer assembly 28. The received signal output by the transducer assembly 28 is supplied to a receiver circuit 40. In the receiver circuit 40, predetermined processing (amplification, detection, A/D conversion) is performed on the received signal, and the signal is output to the analyzer 202 through the controller 36. In the analyzer 202, bone diagnostic values are computed based on the speed or attenuation of ultrasonic waves as in the prior art. These bone diagnostic values are displayed on a display unit, not shown.

The controller 36 controls the transmission and reception of ultrasonic waves, and controls the transport mechanism 42. In particular, the controller 36 of this embodiment controls an aperture adjusting mechanism 44 housed in the transport mechanism 42. When the drive torque has reached a predetermined value, i.e. when the area of the coupler in contact with the body part has reached a predetermined area, the aperture adjusting mechanism 42 stops the transport mechanism 42 from driving the pair of transducer assemblies 28, 30.

A size determining device 45 which determines the size of a foot and which is connected to the controller 36, detects either directly or indirectly whether the foot on the platform is large or small. This determining device 45 may for example be a device which measures the size of the foot using an optical sensor, or a device which determines the type of foot platform by a mechanical sensor. In any case, the size of the foot is automatically determined. The fifth embodiment described hereafter concerns this size determining device 45.

The controller 36 automatically changes the ultrasonic beam cross-sectional area according to the size of foot which is determined.

Figure 9:
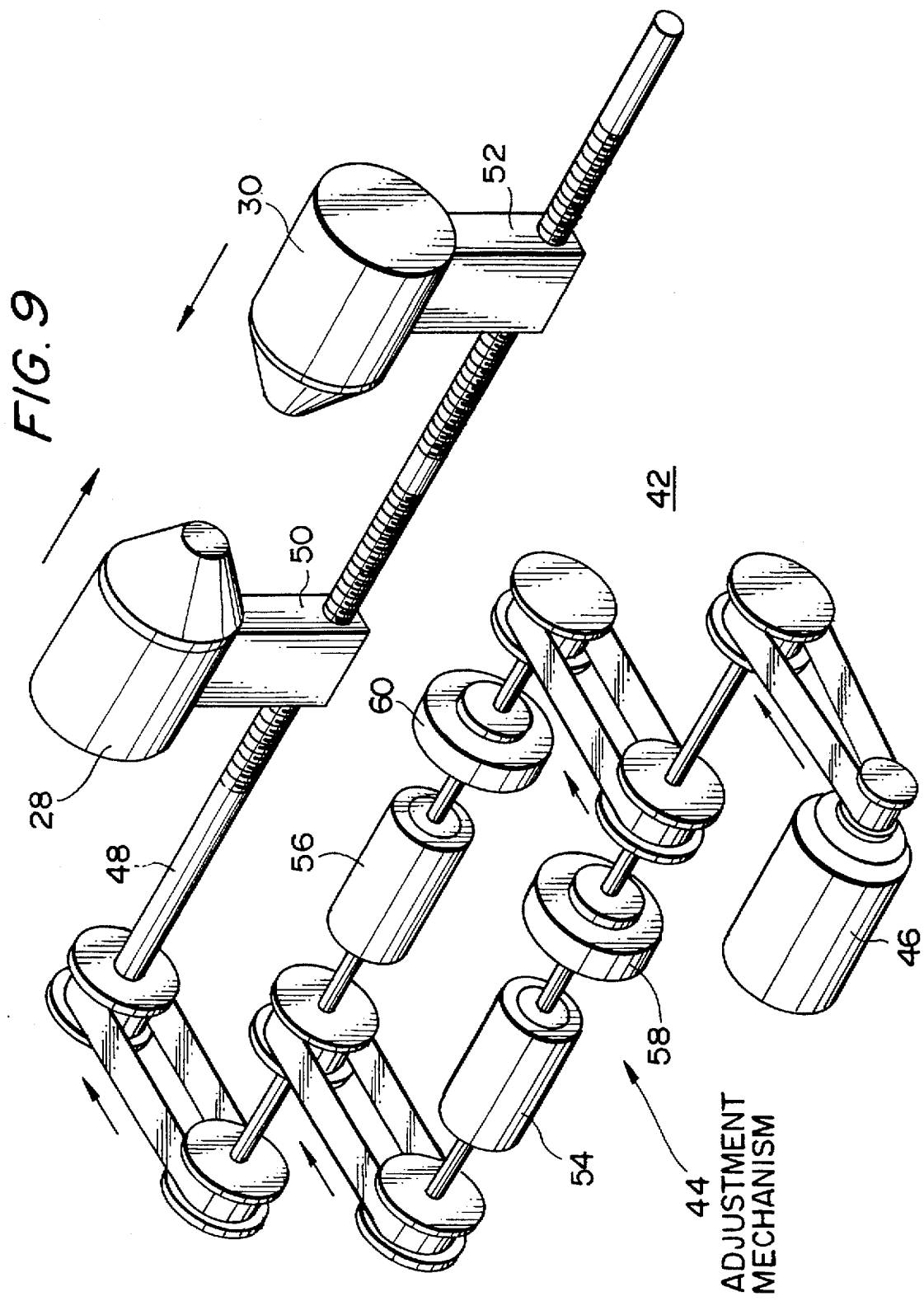
FIG. 9 is a diagram showing a transport mechanism for transporting a pair of transducer assemblies.

FIG. 9 shows the overall construction of the transport mechanism 42. A drive force of a drive motor 46 is transmitted to the aperture adjusting mechanism 44 via a plurality of timing belts and belt pulleys. The drive force transmitted to the aperture adjusting mechanism 44, is then transmitted to a feed screw 48 via a plurality of timing belts and belt pulleys. The feed screw 48 is connected to a movable body 50 carrying the transducer assembly 28, and a movable body 52 carrying the transducer assembly 30. Two spiral grooves are formed in mutually opposite directions in the feed screw 48, and the movable bodies 50, 52 engage respectively with each of these grooves. Hence, when the feed screw 48 is rotated in a forward direction, the pair of transducer assemblies 28, 30 approach each other, and when the feed screw 48 is rotated in a reverse direction, the pair of transducer assemblies 28, 30 move apart.

According to this embodiment, the aperture adjusting mechanism 44 comprises two torque limiters 54, 56 which are arranged in parallel, and two electromagnetic clutches 58, 60 which are respectively connected in series to each of the torque limiters. The two torque limiters 54, 56 have mutually distinct limiting values (torque values when transmission of drive force is interrupted due to slip). For example, the limiting value of the torque limiter 54 may be 200 g·cm, and the limiting value of the torque limiter 56 may be 100 g·cm.

Either one of the electromagnetic clutches 58, 60, is selected by the controller 36. When performing a measurement on an adult's foot (or a person with large feet), the electromagnetic clutch 58 is switched ON, i.e. the torque limiter 54 having a high torque limit is selected. When the drive torque reaches the aforesaid limiting value (200 g·cm), the torque limiter 54 stops transmission of the drive force. When this occurs, the couplers 34 of the pair of transducer assemblies are maintained at their maximum deformation as shown in FIG. 7 so that the ultrasonic beam aperture is large.

On the other hand, when performing ultrasonic measurements on a child's foot (or a person with small feet), the electromagnetic clutch 60 is switched ON, i.e. the torque limiter 56 having a small limiting value functions. When the torque reaches the aforesaid predetermined value (100 g·cm), the torque limiter 56 stops transmission of the drive force. When this occurs, the couplers of the pair of transducer assemblies are maintained with only a slight deformation as shown in FIG. 8 so that the aperture through which the ultrasonic beam passes is small.

Figure 2:
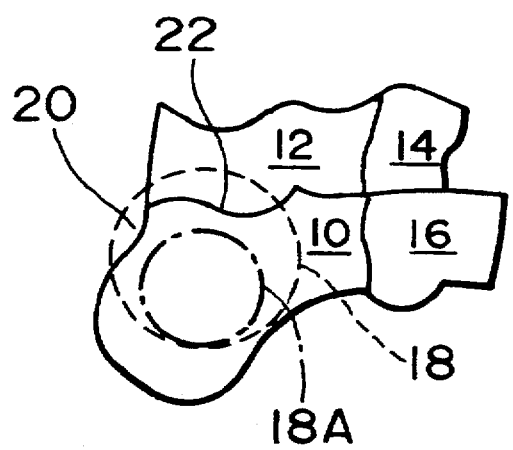
FIG. 2 is a diagram showing an irradiating area of an ultrasonic wave beam when the calcaneous of a child is assessed.

In this way, the width of the ultrasonic beam may be adjusted, so a beam spot having a suitable diameter suitable for the calcaneous 10 of a child may be formed as shown by the symbol 18A of FIG. 2. According to the aforesaid embodiment, either of two torque limiters were selectively used, however three or more torque limiters may be provided to change the aperture area in a plurality of stages.

Next, the overall operation of the bone assessment apparatus according to this invention will be described with reference to FIG. 10.

Figure 1:
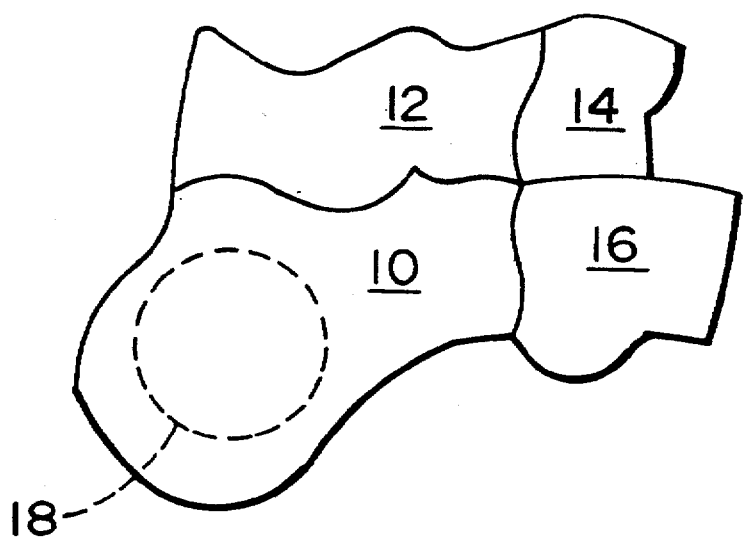
FIG. 1 is a diagram showing an irradiating area of an ultrasonic wave beam when the calcaneous of an adult is assessed.

First, in a step S101, the size of the foot on the foot platform is determined. This is done automatically by the size determining unit 45 shown in FIG. 1, but the size may also be set to any desired value. In a step S102, the controller 36 either increases the width of the ultrasonic beam so as to perform measurements on an adult's foot, or decreases the width of the ultrasonic beam so as to perform measurements on a child's foot.

When it is determined in the step S102 that the foot is of large size, the electromagnetic clutch 58 is selected, i.e. the torque limiter 54 is selected in a step S103, and the pair of ultrasonic transducers 28, 30 are moved together. When the coupler 34 has deformed as shown in FIG. 7, the torque limiter 54 operates, torque transmission is interrupted, and the apparatus is maintained in the state shown in FIG. 7. In this state, ultrasonic waves are transmitted and received. After measurement, the pair of ultrasonic transducers 28, 30 are moved apart.

When on the other hand it is determined in the step S102 that the foot is of small size, the electromagnetic clutch 60 is selected, i.e. the torque limiter 56 is selected in a step S104, and the pair of ultrasonic transducers 28, 30 are moved together. When the coupler 34 has deformed as shown in FIG. 8, the torque limiter 56 operates, torque transmission is interrupted, and the apparatus is maintained in the state shown in FIG. 8. In this state, ultrasonic waves are transmitted and received. After measurement, the pair of ultrasonic transducers 28, 30 are moved apart.

The measurement data are analyzed and bone diagnostic values are computed by the analyzer 202 in a step S105, and these values are displayed in a step S106.

Figure 11:
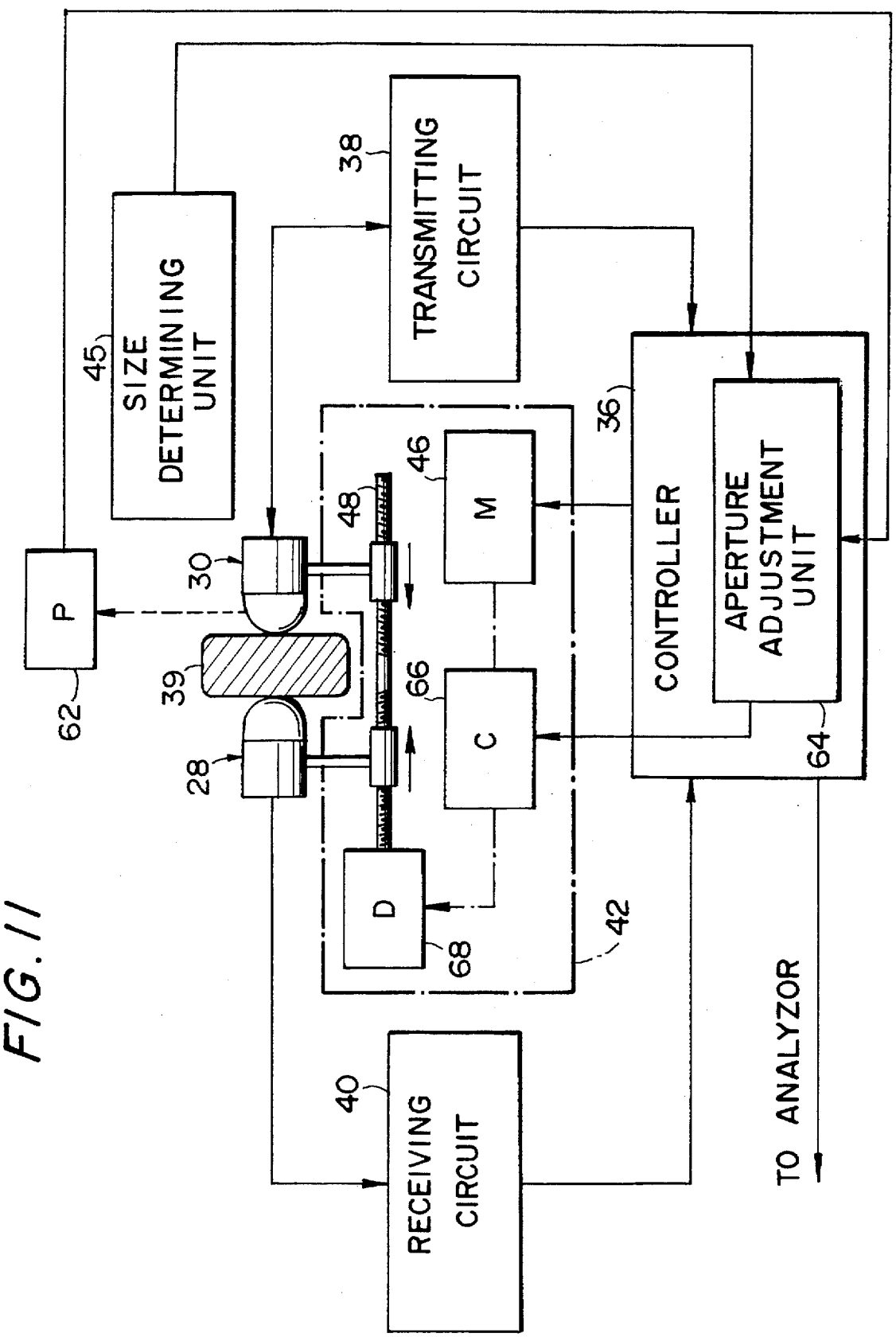
FIG. 11 is a diagram showing a second embodiment of the ultrasonic wave bone assessment apparatus according to this invention.

FIG. 11 shows a second embodiment of this invention. Herein, parts of the construction which are identical to those of the first embodiment shown in FIG. 3 are given the same symbols, and their description is omitted.

Figure 12:
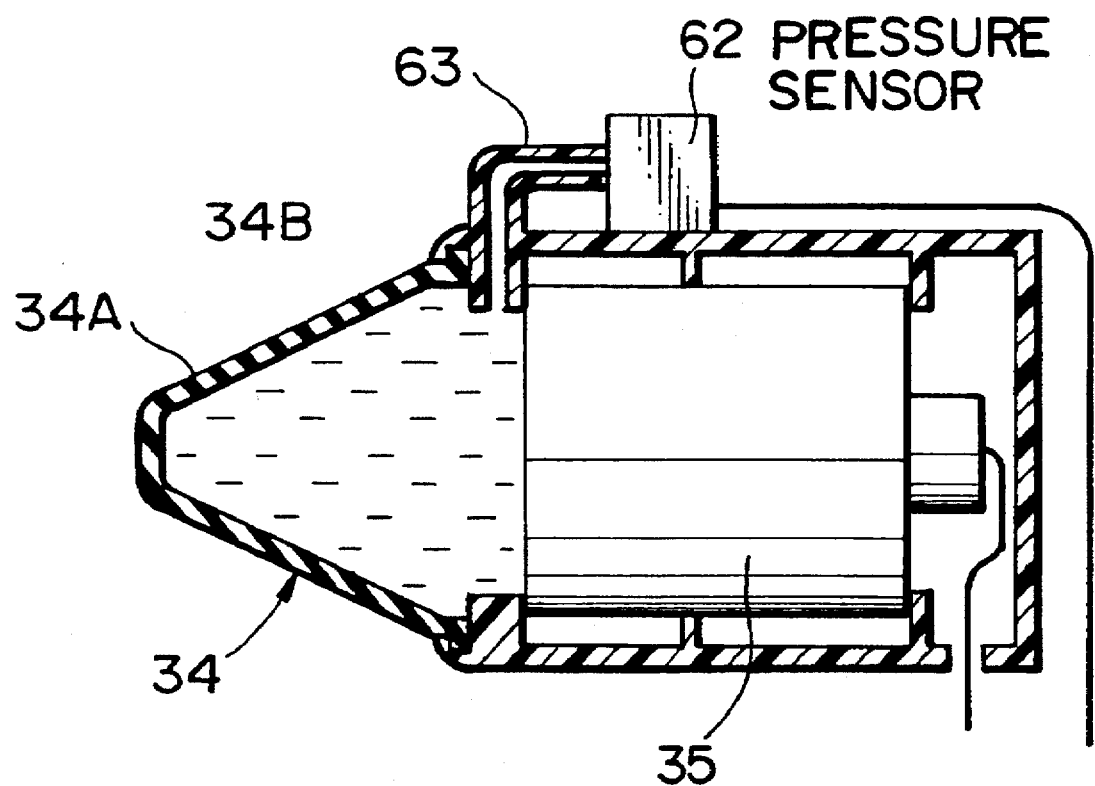
FIG. 12 is a diagram showing a pressure sensor used in the second embodiment according to this invention.

In FIG. 11, a pressure sensor 62 detects the pressure of a coupling liquid in the coupler. FIG. 12 shows an example of this pressure sensor 62. The pressure sensor 62 is set on the assembly body, and a coupling liquid 34B in a membrane 34A is led via a tube 63 to the pressure sensor 62. It may be considered that the pressure of the coupling liquid 34B in the membrane 34A represents the pressure of the coupler on the body part to be measured, so in this way the pressure on the body part can be indirectly measured.

In FIG. 11, an aperture adjusting unit 64 in the controller 36 comprises a plurality of mutually distinct basic pressure values. When the pressure shown by the pressure sensor 62 has reached a basic pressure selected according to the foot size, a command is issued to interrupt transmission of drive torque to an electromagnetic clutch 66. When the electromagnetic clutch 66 is ON, the torque of a motor 46 is transmitted to a mechanism 68 via the electromagnetic clutch 66, and the feed screw 48 is rotated. When on the other hand transmission of drive torque is interrupted by the electromagnetic clutch 66, rotation of the feed screw 48 stops, and the pressure of the transducer assemblies 28, 30 on the foot is set and maintained at a predetermined value. This sets the cross-sectional area of the ultrasonic beam. It will be understood that each of the transducer assemblies 28, 30 may be provided with such a pressure sensor.

In the aforesaid first and second embodiments, both of the transducer assemblies 28, 30 comprise couplers which can freely deform, and the aperture of the ultrasonic beam is adjusted by adjusting the deformation amount of the couplers. The beam spot may be adjusted by providing only the transducer assembly on the transmitting side with an aperture adjusting function. However, by controlling the ultrasonic beam aperture on both the transmitting and receiving sides, the beam width can be more effectively controlled. The beam width can likewise be adjusted by adjusting the deformation of a coupler in a bone assessment apparatus wherein ultrasonic waves are transmitted and received by one transducer assembly.

(2) Embodiment 3

Figure 13:
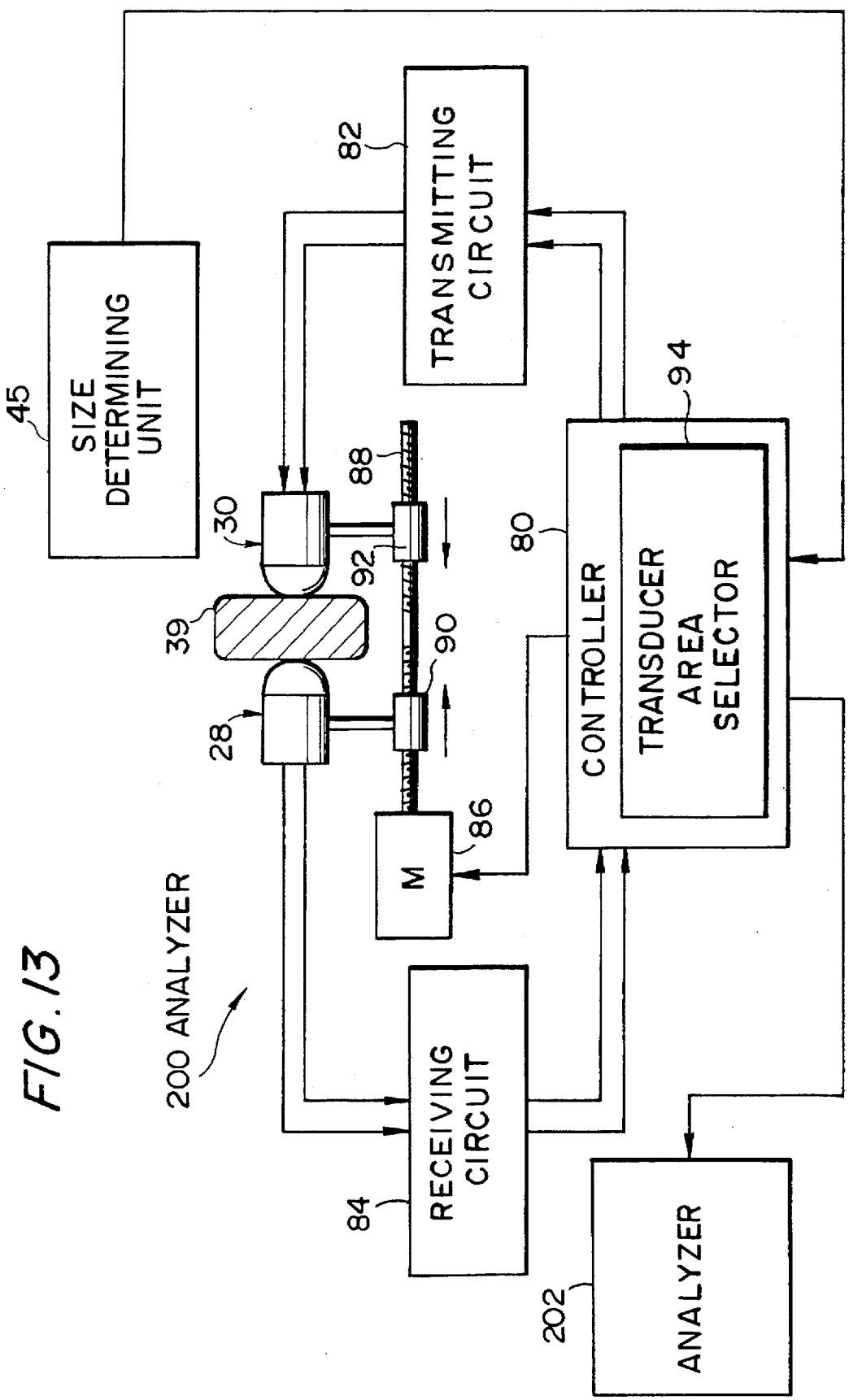
FIG. 13 is a diagram of a third embodiment of the ultrasonic wave bone assessment apparatus according to this invention.

FIG. 13 shows the overall construction of a third embodiment of a bone assessment apparatus according to this invention. This bone assessment apparatus comprises a measuring unit 200 which performs measurements using ultrasonic waves, and an analyzer 202 which analyzes the results measured by the measuring unit and computes bone diagnostic values. The analyzer 202 may for example be a computer.

The external appearance of the measuring unit according to this embodiment is shown in FIG. 4.

The external appearance of the transducer assembly 28 is identical to that of FIG. 5. The two transducer assemblies 28, 30 have an identical form and construction.

Figure 14:
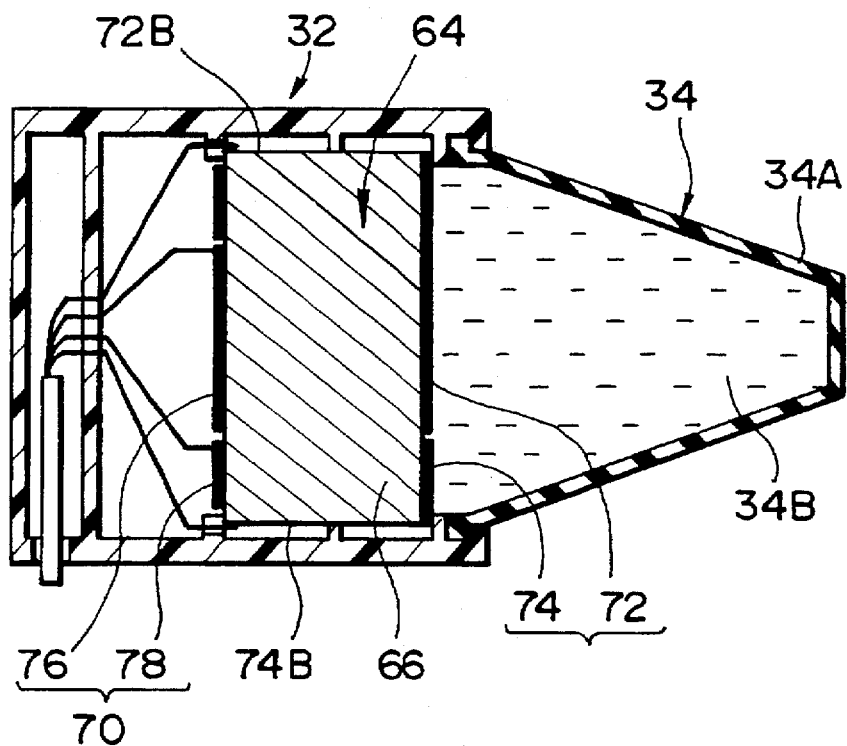
FIG. 14 is a view in section of a transducer assembly according to the third embodiment.
Figure 15:
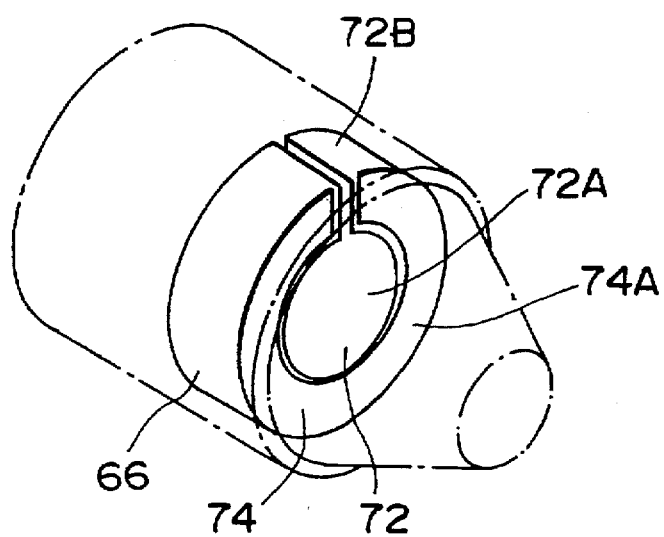
FIG. 15 is a perspective transparent view of a transducer assembly according to the third embodiment.

FIG. 14 shows a view in section of the transducer assembly according to the third embodiment. As shown in FIG. 14, according to this embodiment, the coupler 34 comprises a membrane 34A which defines its external contour, and a coupling liquid 34B (e.g. castor oil) which fills its interior. The coupler 34 elastically deforms according to the contact pressure on a body part to be measured. For example, the diameter of the apical surface of the coupler 34 is 1 cm, its diameter on the transducer side is 2.5 cm, and its length (height) is approx. 2–3 cm. According to this embodiment, couplers of different shapes may be used.

An ultrasonic transducer 64 which transmits and receives ultrasonic waves is provided in the chassis 32. As shown by the transparent perspective view of FIG. 14, the ultrasonic transducer 64 comprises an annular array of ultrasonic transducer elements. Specifically, the ultrasonic transducer 64 comprises a single circular piece of a piezoelectric material 66, a front electrode 68 formed in front of the piezoelectric material 66, and a rear electrode 70 formed behind the piezoelectric material 66.

The front electrode 68 comprises a center electrode element 72 and a ring-shaped electrode element 74, these elements being electrically isolated from each other. The center electrode element 72 comprises a circular area 72A, and an area 72B extending from the edge of the circular area 72A backwards along the piezoelectric material 66. The ring-shaped electrode element 74 comprises a ring-shaped area 74A formed in the shape of a ring around the circular area 72A, and an area 74B extending from the edge of the ring-shaped area 74A backwards along the piezoelectric material 66 (FIG. 14).

The rear electrode 70 comprises a circular center electrode element 76 and a ring-shaped electrode element 78 formed in a ring-shape around the central element 76. Signal leads are separately connected to the central electrode element 72, ring-shaped electrode element 74, center electrode element 76 and ring-shaped electrode element 78 so that each electrode element can be electrically selected.

The circular area 72A in the front electrode 68 and the center electrode element 76 in the rear electrode 70 have an identical diameter. Also, the ring-shaped area 74A in the front electrode 68 and the ring-shaped element 78 in the rear electrode have an identical shape. The ultrasonic transducer 64 is surrounded (rear and side spaces) by an oil having insulating properties, e.g. castor oil.

Returning to FIG. 13, a transmitting circuit 82 sends a transmission drive signal to the transducer assembly 30 based on a trigger signal from a controller 80. Ultrasonic waves (ultrasonic pulses) are thereby transmitted from the transducer assembly 30 to the body part 39. When they pass through the body part 39, the characteristics of the ultrasonic waves change, and these waves are received by the transducer assembly 28. The received signal output by the ultrasonic transducer 28 is supplied to a receiver circuit 84. In the receiver circuit 84, predetermined processing (amplification, detection, A/D conversion) is performed on the received signal, and the signal is output to the analyzer 202 through the controller 80. In the analyzer 202, bone diagnostic values are computed based on the speed or attenuation of ultrasonic waves as in the prior art. These bone diagnostic values are displayed on a display unit, not shown.

The controller 80 controls the transmission and reception of ultrasonic waves, and controls a transport mechanism 86.

The transport mechanism 86 comprises a drive motor, not shown, a torque limiter, not shown, and a feed screw 88. The feed screw 88 is connected to a movable body 90 carrying the transducer assembly 28, and a movable body 92 carrying the transducer assembly 30. Two spiral grooves are formed in mutually opposite directions in the feed screw 88, and the movable bodies 90, 92 engage respectively with each of these grooves. Hence, when the feed screw 88 is rotated in a forward direction, the pair of transducer assemblies 28, 30 approach each other, and when the feed screw 88 is rotated in a reverse direction, the pair of transducer assemblies 28, 30 move apart.

When the pressure of the pair of transducer assemblies 28, 30 on the body part reaches a predetermined value, the torque limiter stops transmission of drive torque from the drive motor. The couplers 34 shown in FIG. 14 are then fully deformed, and provide a reliable path for propagation of ultrasonic waves.

The controller 80 according to this embodiment comprises a vibrating area change-over unit 94. This vibrating area change-over unit 94 changes the vibrating area of the ultrasonic transducer 64 by selecting a number of vibrating elements (i.e. electrode elements).

Specifically, in the adult measurement mode, the vibrating area change-over unit 94 activates the center electrode element 72 and ring-shaped electrode element 74 which form the front electrode 68, and activates the center electrode element 76 and ring-shaped electrode element 78 forming the rear electrode 70. In other words, the entire front electrode 68 and rear electrode 70 function as transmitting or receiving electrodes so that the whole of the piezoelectric material 66 vibrates. The cross-sectional area of the ultrasonic beam is thereby increased.

Conversely in the child measurement mode, the vibrating area change-over unit 94 activates only the center electrode element 72 forming part of the front electrode 68 and the center electrode element 76 forming part of the rear electrode 70. In other words, only the center parts of the front electrode 68 and rear electrode 70 function as transmitting or receiving electrodes so that the vibrating area of the piezoelectric material 66 is limited. The cross-sectional area of the ultrasonic beam is thereby decreased.

The controller 80 is connected to a size determining device 45 which determines the size of a foot. This size determining device 45 detects either directly or indirectly whether the foot on the foot platform is large or small. This determining device 45 may for example be a device which measures the size of the foot using an optical sensor, or a device which determines the type of foot platform by a mechanical sensor. In any case, the size of the foot is automatically determined. The controller 80 may of course also be supplied with any desired size. Hence, the vibrating area change-over unit 94 changes over the vibrating area based on the size of the foot which is determined.

In this way, the width of the ultrasonic beam may be changed over between two values, and a beam spot having a suitable diameter suitable for the calcaneous 10 of a child may be formed as shown by the symbol 18A of FIG. 2. In the above description, either of two vibrating areas were selected, however a selection may be made between three or more vibrating areas so as to change the ultrasonic beam aperture area in a plurality of stages.

Figure 10:
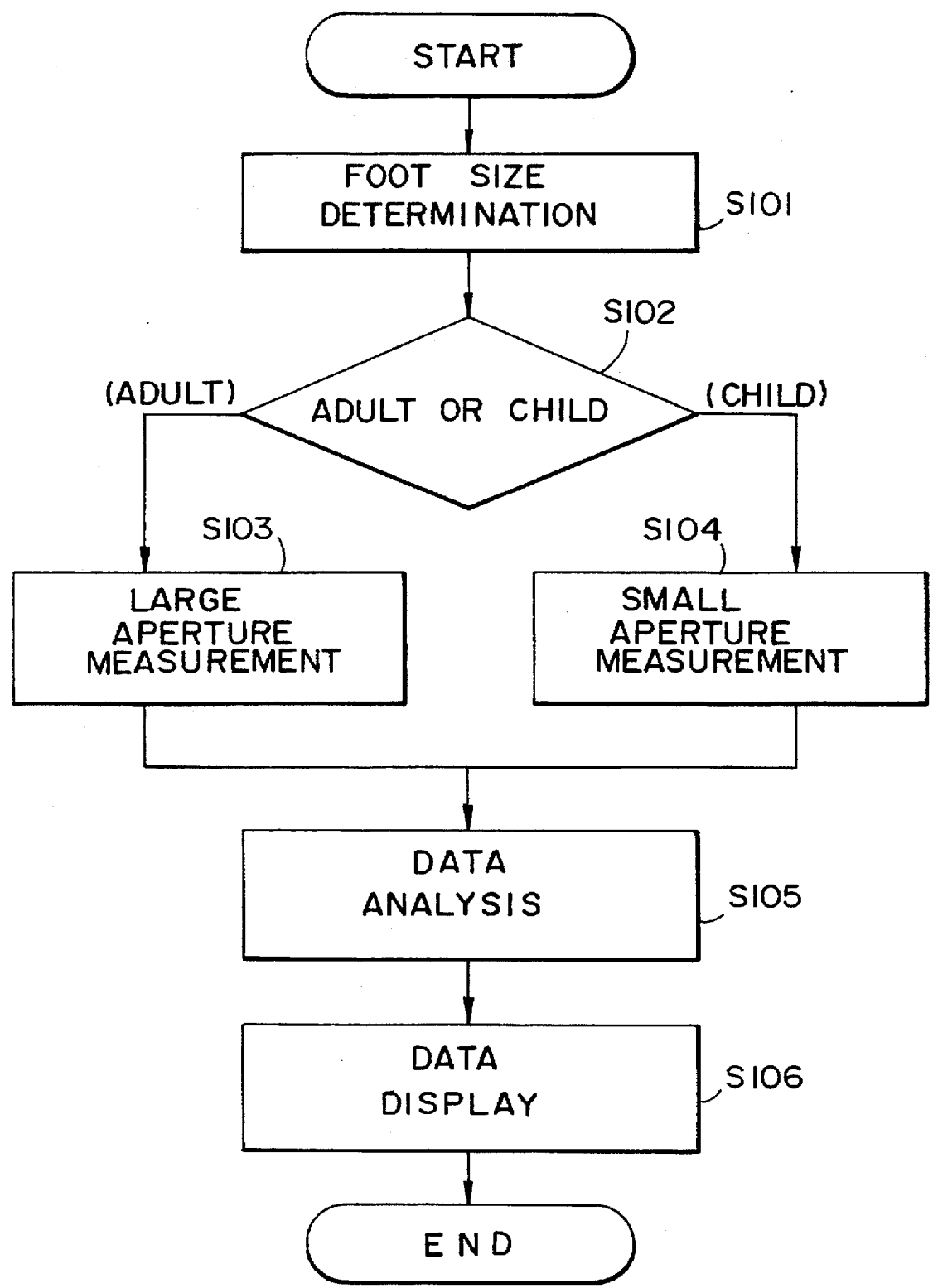
FIG. 10 is a flowchart showing different steps when bone is assessed using the ultrasonic wave bone assessment apparatus according to this invention.

The overall operation of the ultrasonic wave bone assessment apparatus according to the third embodiment is substantially the same as that shown in FIG. 10.

First, in the step S101, the size of the foot on the foot platform is determined. This is done automatically by the size determining unit 45 shown in FIG. 1, but any desired size may be set. In the step S102, the controller 80 either increases the width of the ultrasonic beam so as to perform measurements on an adult's foot, or decreases the width of the ultrasonic beam to perform measurements on a child's foot.

The body part is then inserted between the pair of transducer assemblies 28, 30, and is gripped between them.

When it is determined in the step S102 that the foot is of large size, all the electrode elements are selected (i.e. the entire transducer is selected) in the step S103 so as to set a large vibrating area or large aperture, and measurements are made using a wide ultrasonic beam. On the other hand when it is determined in the step S102 that the foot is of small size, only a part of the electrode elements (i.e. a partial area) is selected in the step S104 so as to set a small vibrating area or large aperture, and measurements are made using a narrow ultrasonic beam.

The measurement data are analyzed and bone diagnostic values are computed in the step S105, and these values are displayed in the step S106.

According to the aforesaid embodiment, an annular array transducer was used, but a transducer comprising elements disposed in a two-dimensional array may be used instead. Also according to the aforesaid embodiment, the vibrating area was set on both the transmitting side and receiving side, however the vibrating area may be set on only the transmitting side.

The change-over of vibrating area may also be performed in a bone assessment apparatus wherein an ultrasonic beam is transmitted and received by one transducer assembly.

(3) Embodiment 4

Figure 16:
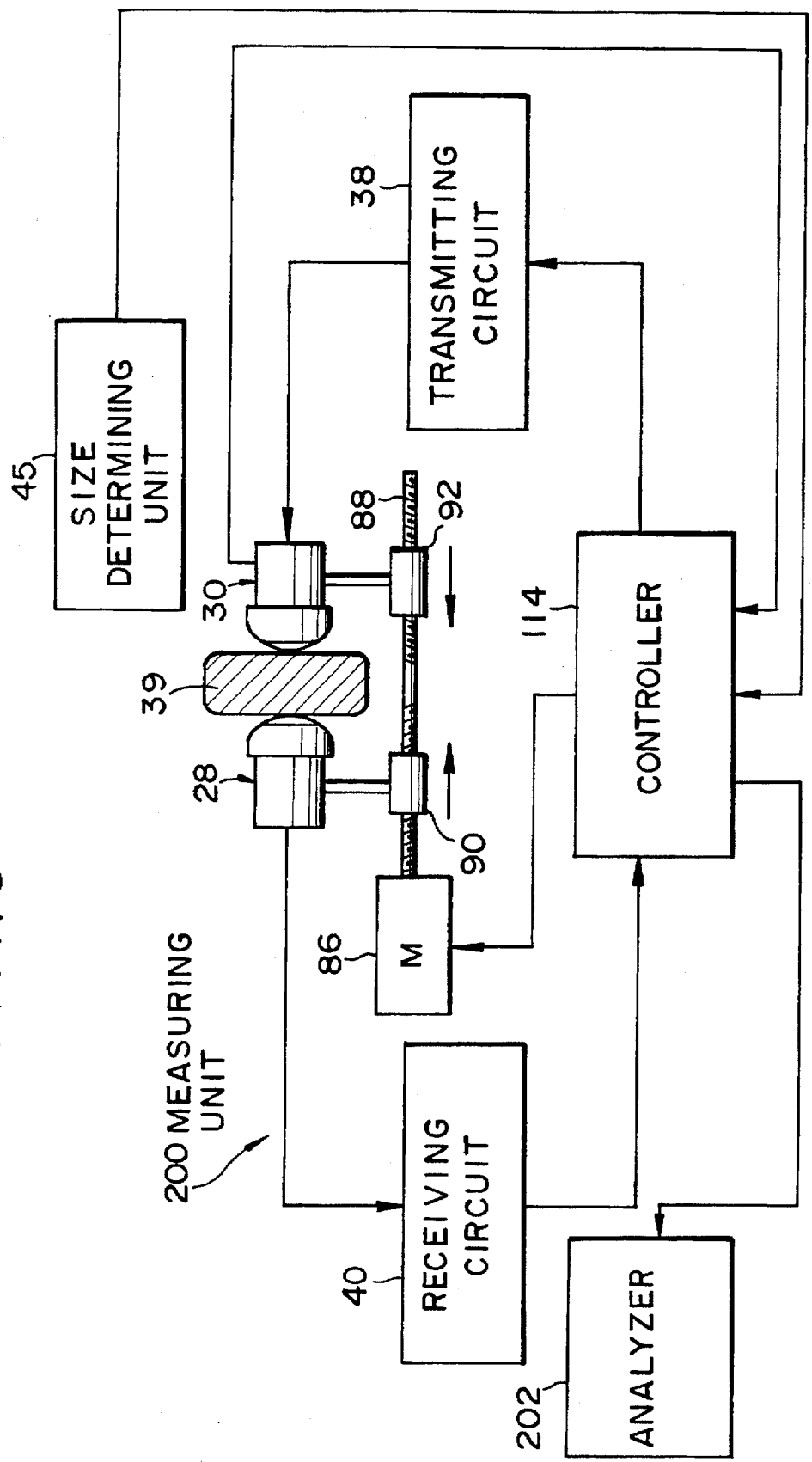
FIG. 16 is a diagram showing a fourth embodiment of the ultrasonic wave bone assessment apparatus according to this invention.

FIG. 16 shows a fourth embodiment of the ultrasonic wave bone assessment apparatus according to this invention. This apparatus comprises a measuring unit 200 which performs measurements using ultrasonic waves, and an analyzer 202 which analyzes the results obtained by the measuring unit and computes bone diagnostic values. The analyzer 202 may for example be a computer.

The external appearance of the measuring unit 200 is identical to that shown in FIG. 4.

Figure 17:
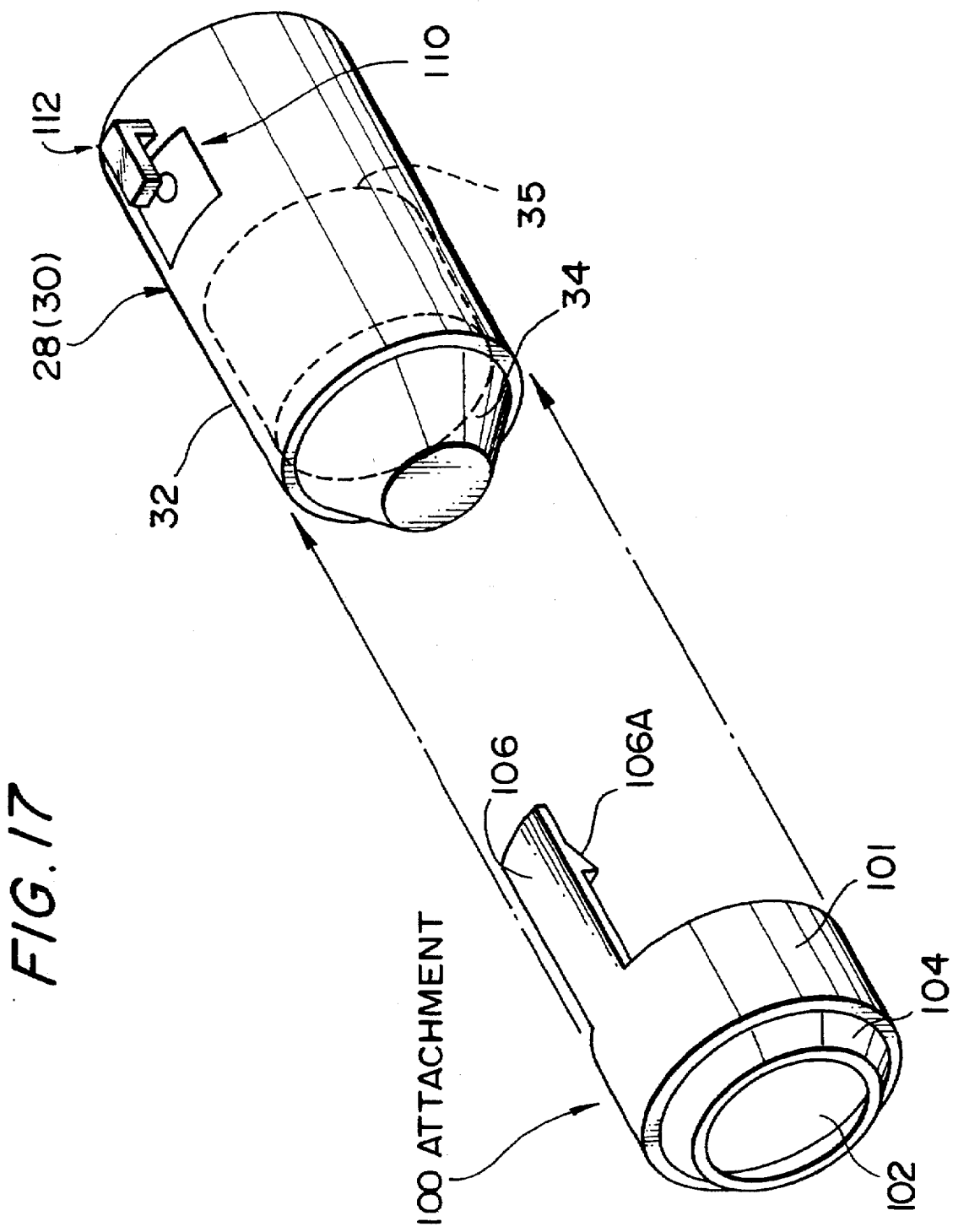
FIG. 17 is an external view of a transducer assembly and attachment according to the fourth embodiment.

FIG. 17 shows the external appearance of the transducer assembly 28 and an attachment 100 which can be freely attached to or detached from the assembly 28. According to this embodiment, the two transducer assemblies 28, 30 have an identical form and construction.

The transducer assembly 28 comprises the chassis 32 housing a relatively large single ultrasonic transducer 35, and a substantially conical coupler 34 (having a trapezoidal cross-section) provided in front of the chassis. The coupler 34 is provided to enable good ultrasonic wave propagation between the transducer 35 and the body, and it is capable of elastic deformation.

The attachment 100 comprises an envelope 101, a ring-shaped member 104 situated at its front and a hook 106 which extends from the envelope 101. An aperture 102 is formed in the ring-shaped member 104, the cross-sectional area of an ultrasonic wave beam being limited by this aperture 102. The ring-shaped member 104 is capable of elastic deformation, and comprises a material which absorbs and blocks ultrasonic waves (e.g. rubber filled with numerous minute bubbles). The ring-shaped member 104 absorbs and blocks ultrasonic waves at more than a certain distance (corresponding to the radius of the aperture 102) from the beam center.

A claw 106A is formed on the hook 106, and a groove 110 with which the claw 106A engages is formed on the lateral surface of the chassis 32.

The transducer assembly 28 also comprises a clip-on sensor 112.

Figure 18:
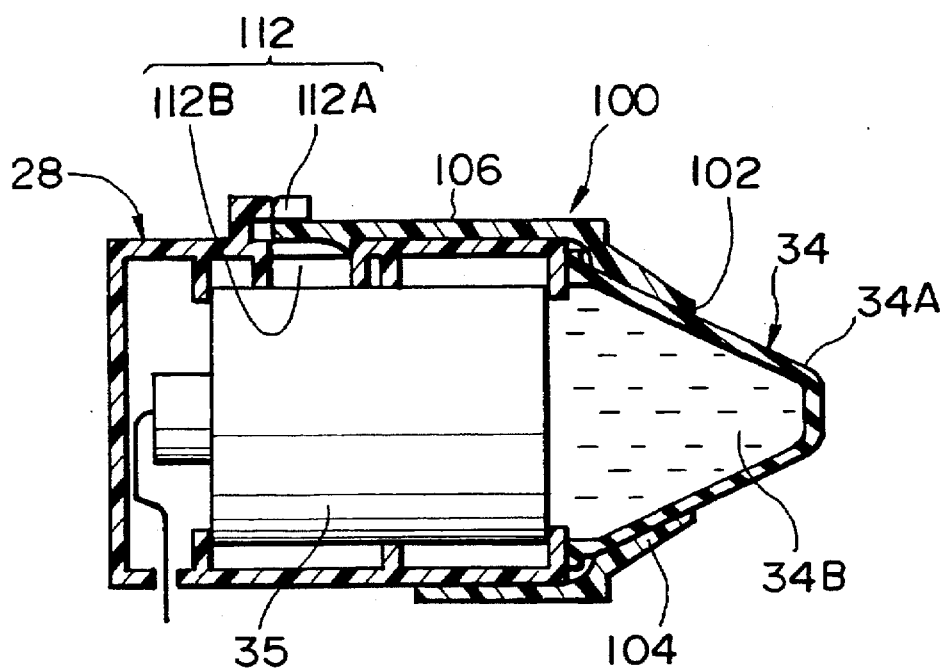
FIG. 18 is a view in section of a transducer assembly.

FIG. 18 is a view in section of the transducer assembly 28 with the attachment 100 fitted. The coupler 34 comprises a membrane 34A which defines its external contour, and a coupling liquid 34B (e.g. castor oil) which fills its interior. The coupler 34 elastically deforms according to the contact pressure on the body part to be measured. For example, the diameter of the apical surface of the coupler 34 is 1 cm, its diameter on the transducer side is 2.5 cm, and its length (height) is approx. 2–3 cm. According to this embodiment, couplers of different shapes may of course be used. As shown in FIG. 18, when the attachment is fitted, the coupler 34 projects from the aperture 102. In this state, the inner surface of the ring-shaped member 104 is in intimate contact with the membrane 34A of the coupler 34.

Specifically, the aforesaid clip-on sensor 112 comprises a light emitting element 112B and a photosensitive element 112A. When the hook 106 is not inserted in the groove 110, light emitted by the light emitting element 112B is detected by the photosensitive element 112A. When on the other hand the attachment 100 is properly fitted as shown in FIG. 18, the hook 106 is interposed between the light emitting element 112B and photosensitive element 112A so that the light from the element 112B is blocked.

Figure 19:
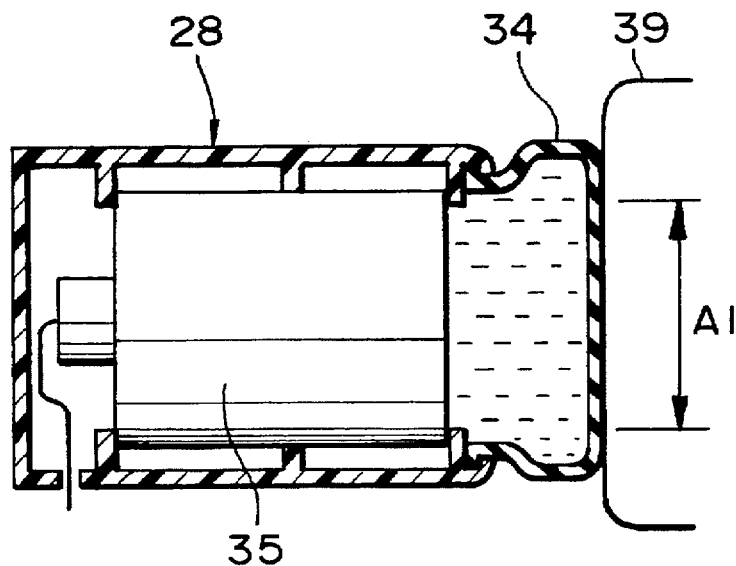
FIG. 19 is a diagram showing an ultrasonic beam aperture when an attachment is not fitted.

When the attachment 100 is not fitted to the transducer assembly 28 and the transducer assembly 28 presses on the body 39 with a constant pressure, the coupler 34 deforms so that the large contact area (ultrasonic beam aperture) A1 is obtained, as shown in FIG. 19. The size of this aperture A1 is equal to or greater than the area of the vibrating surface of the ultrasonic transducer 35.

Figure 20:
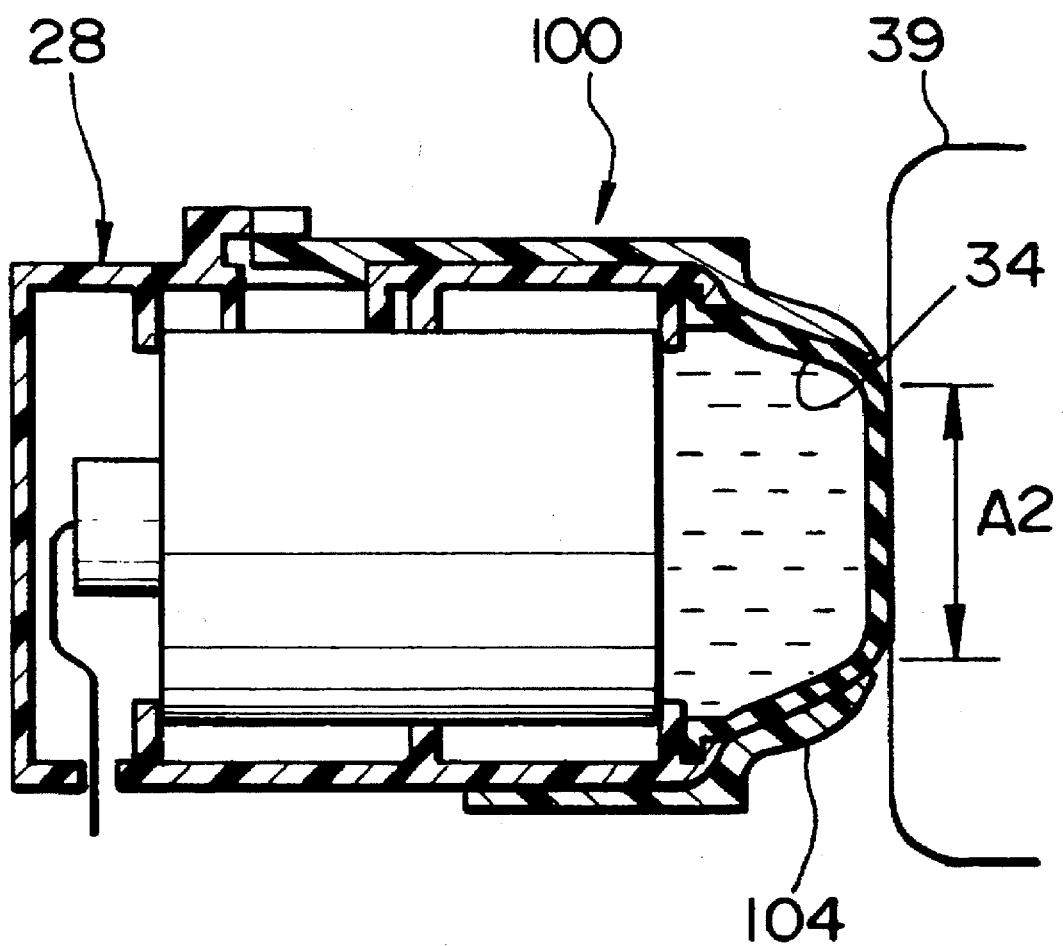
FIG. 20 is a diagram showing an ultrasonic beam aperture when an attachment is fitted.

When the attachment 100 is fitted to the transducer assembly 28 and the assembly 28 presses on the body 39 with a constant pressure, the coupler 34 starts to deform, however its elastic deformation is limited by the ring-shaped member 104 of the attachment 100 as shown in FIG. 20, so the contact area (ultrasonic beam aperture) A2 which is smaller than the area A1 shown in FIG. 19 is obtained. The ring-shaped member 104 comprises a material such as rubber which is itself capable of slight deformation, so any pain or discomfort when the member 104 comes in contact with the body is alleviated. The contact pressure of the transducer assembly 28 on the body is controlled so that the set contact area is always obtained.

When a bone assessment is performed on an adult's bone, the attachment 100 is not fitted so that the beam cross-sectional area is increased when making ultrasonic measurements. On the other hand, when a bone assessment is performed on a child's bone, the attachment 100 is fitted so that the beam cross-sectional area is decreased when making ultrasonic measurements.

Returning to FIG. 16, a transmitting circuit 38 sends a transmission drive signal to the transducer assembly 30 based on a trigger signal from a controller 114. Ultrasonic waves (ultrasonic pulses) are thereby transmitted from the transducer assembly 30 to the body part 39. When they pass through the body part 39, the characteristics of the ultrasonic waves change, and these waves are received by the transducer assembly 28. The received signal output by the ultrasonic transducer 28 is supplied to the receiver circuit 40. In the receiver circuit 40, predetermined processing (amplification, detection, A/D conversion) is performed on the received signal, and the signal is output to the analyzer 202 through a controller 114. In the analyzer 202, bone diagnostic values are computed based on the speed or attenuation of ultrasonic waves as in the prior art. These bone diagnostic values are displayed on a display unit, not shown.

The controller 114 controls the transmission and reception of ultrasonic waves, and controls the transport mechanism 86.

The transport mechanism 86 comprises a drive motor, not shown, a torque limiter, not shown, and the feed screw 88. The feed screw 88 is connected to the movable body 90 provided with the transducer assembly 28, and the movable body 92 provided with the transducer assembly 30. Two spiral grooves are formed in mutually opposite directions in the feed screw 88, and the movable bodies 90, 92 engage respectively with each of these grooves. Hence, when the feed screw 88 is rotated in a forward direction, the pair of transducer assemblies 28, 30 approach each other, and when the feed screw 88 is rotated in a reverse direction, the pair of transducer assemblies 28, 30 move apart.

When the pressure of the pair of transducer assemblies 28, 30 on the body part reaches a predetermined value, the torque limiter stops transmission of drive torque from the drive motor.

The controller 114 is connected to a size determining device 45 which determines the size of a foot. This size determining device 45 detects either directly or indirectly whether the foot on the foot platform is large or small. This determining device 45 may for example be a device which measures the size of the foot using an optical sensor, or a device which determines the type of foot platform by a mechanical sensor. In any case, the size of the foot is automatically determined. The controller 114 may of course also be supplied with any desired size.

When the determined size is small, the controller 114 displays a message on a display, not shown, advising the user to fit the attachment. When a measurement is performed without fitting the attachment although the determined foot size is small, or when a measurement is performed when the attachment is fitted although the determined foot size is large, the controller 114 outputs an alarm.

Information concerning whether bone measurements were performed with or without the attachment are stored for each patient in a memory provided in the controller 114 based on the output of the attachment sensor. Bone assessment conditions can therefore be stored. The controller 114 also has a function for automatically determining, by comparing past and present measurements for a given patient, that there is an inconsistency in the presence or absence of the attachment, and outputting an alarm indicating such an inconsistency.

As described above, the width of the ultrasonic beam may be changed in two stages by fitting and removing the attachment, so a suitable beam spot for performing measurements on the child's calcaneous 10 can be formed as shown by 18A in FIG. 2. Also by providing different types of attachment having apertures of different sizes, the ultrasonic beam aperture area may be varied in a plurality of stages.

The overall operation of the bone assessment apparatus according to the fourth embodiment will now be described.

First, in the step S101, the size of the foot on the foot platform is determined. This is done automatically by the size determining unit 45 shown in FIG. 16 but any desired size may be set. In both cases, it is determined whether or not the attachment should be fitted. This determination may be performed by the controller, but may also be performed manually. In the step S102, a selection is made to perform measurements on an adult's foot, i.e. increase the ultrasonic beam width, or to perform measurements on a child's foot, i.e. decrease the ultrasonic beam width. Subsequently, the body part is inserted between the pair of transducer assemblies 28, 30, and is gripped between them.

When it is determined in the step S102 that the foot is large, ultrasonic measurements are performed without fitting the attachment in the step S103. In other words, a large aperture is set, and measurements are made with a wide ultrasonic beam. When on the other hand it is determined in the step S102 that the foot is small, the attachment is fitted, a small aperture is set and measurements are performed with a narrow ultrasonic beam in the step S104. In the step S105, the measurement data is analyzed so as to compute bone diagnostic values, and in the step S106, these values are displayed.

The attachment is fitted to either the transmitting transducer or the receiving transducer, or to both. Also according to the above embodiment, bone assessments were performed using ultrasonic waves, however the invention may likewise be applied to an apparatus which performs bone assessments using X rays or other measuring waves. Further, this invention may be applied to a bone assessment apparatus wherein transmitting and receiving of ultrasonic waves is performed by one transducer assembly.

(4) Embodiment 5

Figure 21:
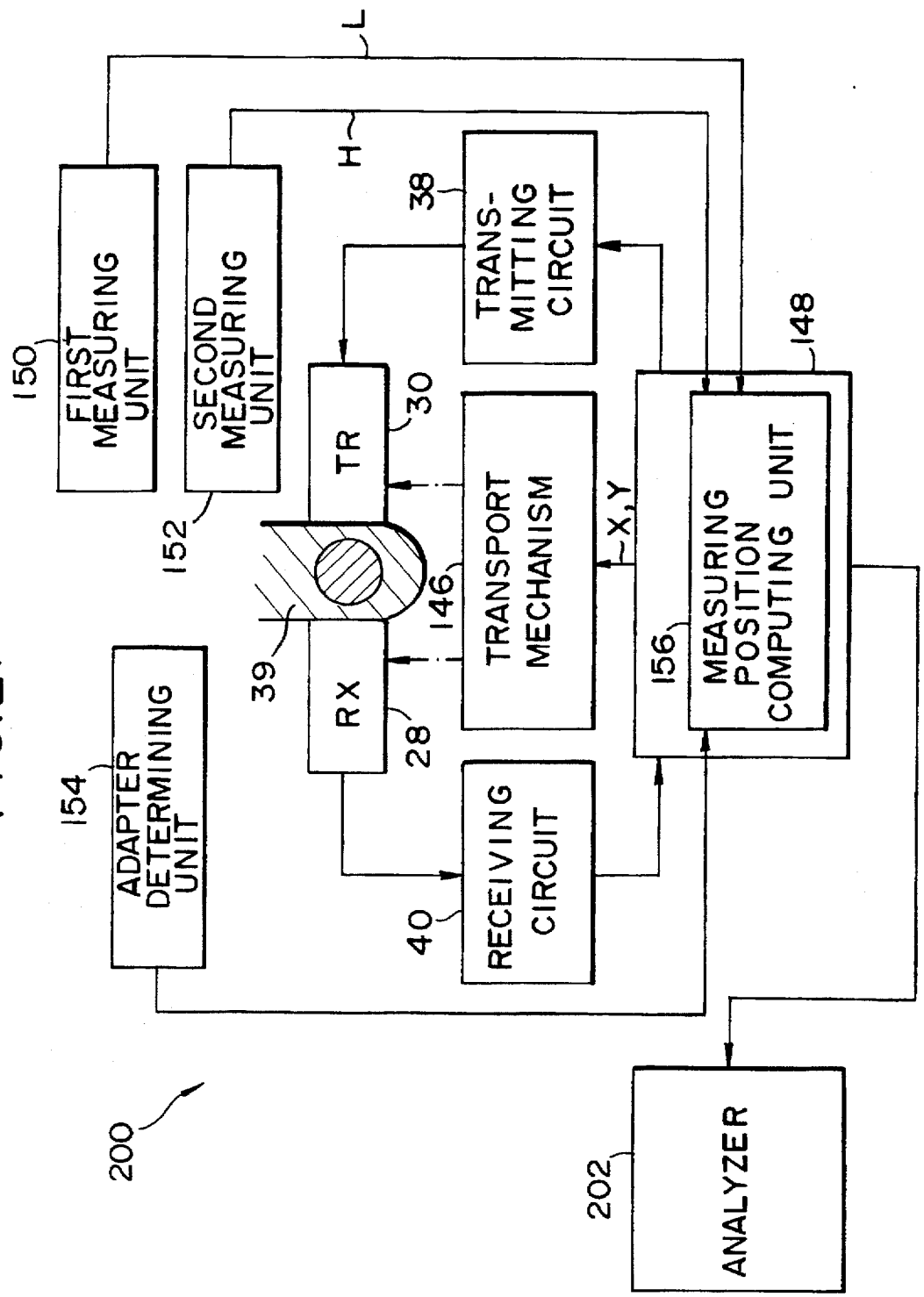
FIG. 21 is a block diagram of a fifth embodiment of the ultrasonic wave bone assessment apparatus according to this invention.

FIG. 21 is a block diagram showing the overall construction of a bone assessment apparatus according to a fifth embodiment of this invention. This apparatus performs an assessment of bone in a living organism by transmitting and receiving ultrasonic waves to the organism, however this invention may also be applied to an apparatus which performs bone assessment using X rays.

The apparatus shown in FIG. 21 broadly comprises the measuring unit 200 which transmits and receives ultrasonic waves, and the analyzer 202 which computes bone diagnostic values based on the results obtained by transmitting and receiving these ultrasonic waves. Each one of the pair of transducer assemblies 28, 30 comprising ultrasonic transducers is disposed on either side of the foot 39 which is to be measured. The transducer assembly 30 is used for transmitting, and the transmitter assembly 28 is used for receiving.

According to this embodiment, these transducer assemblies 28, 30 may be transported in three dimensions by a transport mechanism 146 so that the measurement point may be freely adjusted. A controller 148 controls the operation of the measuring unit 200. A transmission trigger output by the controller 148 is supplied to a transmitting circuit 38, and a signal transmitted by the transmitting circuit 38 is supplied to the transducer assembly 30. An ultrasonic wave is then transmitted by the transducer assembly 30 to the foot 39, and after passing through the foot 39, the wave is received by the transducer assembly 28. A received signal from the transducer assembly 28 is sent to the controller 148 via the receiver circuit 40. The receiver circuit 40 comprises for example an amplifier and detector, etc. The received signal input to the controller 148 is sent to the analyzer 202, and bone diagnostic values are computed in the analyzer 202.

The controller 148 comprises a measuring position computing unit 156. This computing unit 156 determines a suitable measuring position based on the size of the foot, and outputs measuring position coordinates (X, Y) representing this position to the transport mechanism 146. The transport mechanism 146 then moves the pair of transducer assemblies 28, 30 in the X direction or Y direction so that the center of the ultrasonic wave beam coincides with the measuring point that has been determined (FIG. 22).

An identifying result output by an adapter identifier 154 is input to the measuring position computing unit 156. As described hereafter, this adapter identifier 154 identifies the type of adapter 26 used as the foot platform fitted to the measuring unit 200 (FIG. 22), and the determination result is used in computing the measuring position.

Measurement signals from a first measuring device 150 and second measuring device 152 are also input to this measuring position computing unit 156. Based on these measurement signals, the measuring position computing unit 156 determines a suitable measuring position as described hereabove. This will now be described in more detail.

Figure 22:
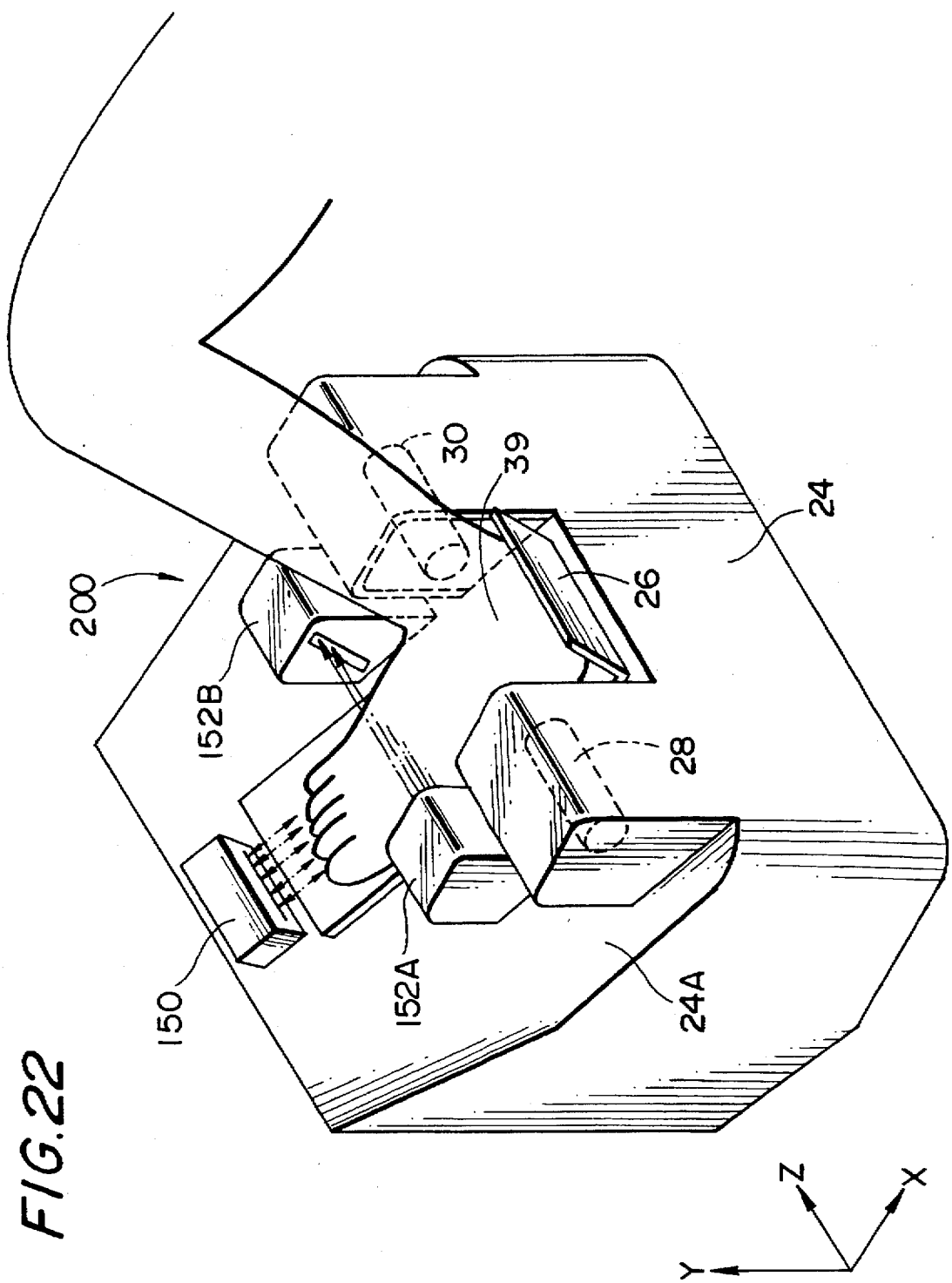
FIG. 22 is a perspective view of a measuring unit according to the fifth embodiment.

FIG. 22 shows a perspective view of the measuring unit 200. The adapter 26 can be freely attached to or detached from the upper surface 24A of the chassis 24 as a foot platform. The adapter 26 for use with adults is relatively thin, while the adapter 26 for use with children is relatively thick. Adapters 26 of different sizes may also be used.

The foot 39 is placed on the adapter 26, and the pair of transducer assemblies 28, 30 is disposed on either side of the adapter 26 facing each other. When performing a bone assessment, the transducer assemblies 28, 30 move in the Z direction, i.e. the direction in which they approach each other, and as a result the calcaneous which is to be measured is gripped by the pair of transducer assemblies 28, 30. In this state, ultrasonic waves are transmitted and received.

A planta length detector 150 is fixed as a first measuring device to the measuring unit 200 of this embodiment as shown in FIG. 22. This detector 150 is installed adjacent to the toes of the foot 39 supported on the adapter 26. The length from the detector 150 to the tips of the toes is measured by scanning with a laser beam in the direction of the Z axis, and the length of the planta of the foot (length from the rear edge of the heel to the tip of the longest toe) is computed based on the minimum value of this measured result.

This detector 150 comprises a laser sensor, but another sensor may be used instead of this optical sensor.

The length of the planta is used as a parameter to determine the measuring position, hence the distance to the tip of a specific toe may also be defined as the length of the planta. Alternatively, the size of another part indicative of the size of the foot may be measured and used as a parameter.

An instep height detector 152 is provided on the upper surface 24A of the chassis 24 as a second measuring device to measure the height of the instep of the foot 39, as shown in FIG. 22. Specifically, this detector 152 comprises a light emitting device 152A and photosensitive device 152B, and the height of the instep of the foot is determined from the width of laser beams received when a plurality of laser beams are transmitted (/received) between the light emitting device 152A and photosensitive device 152B. According to this embodiment, the detector 152 is fixed to the upper surface 24A, however a mechanism may also be provided for shifting the light emitting device 152A and photosensitive device 152B in the direction of the toes or the direction of the heel based for example on the measured results obtained by the first measuring device 150. If this construction is adopted, the height of the instep of the foot may be determined more objectively.

Figure 23:
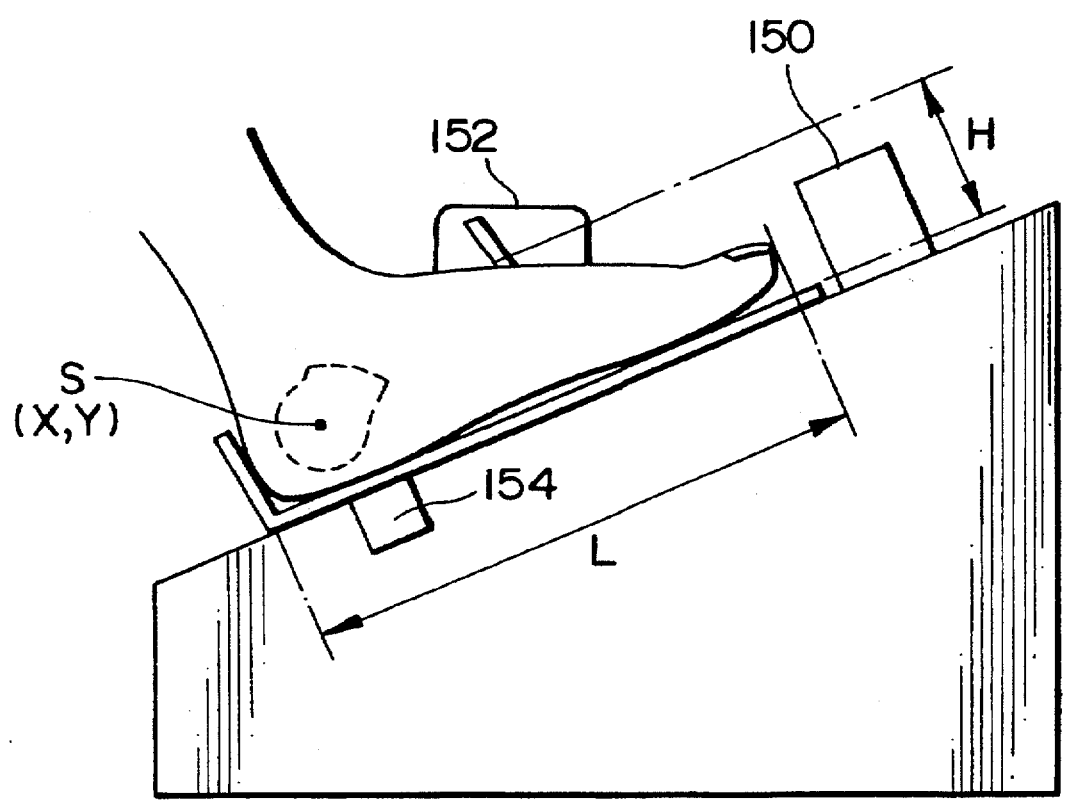
FIG. 23 is a diagram showing a method of measuring the size of a foot.

FIG. 23 shows the length L of the planta and height H of the instep measured by the first measuring device 150 and second measuring device 152. The length L of the planta is defined as the length from the rear edge of the heel to the tips of the toes, and the height H of the instep is defined as the height of the instep at a position where the second measuring device is installed. The length L of the planta and height H of the instep so determined are used as parameters to compute the measurement coordinates X, Y, and as a result, the center of the calcaneous may be estimated as a measurement position S. According to this embodiment, the adapter identifier 154 is provided as shown in FIG. 23 so that the type of adapter fitted is automatically determined. In computing the length L of the planta and height H of the instep, the form of the adapter used is taken into account.

Next, the operation of the measuring unit will be described with reference to FIG. 24.

First, in the step S101, the type of the adapter 26 set in the measuring unit 200 is determined by the adapter identifier 154. Next, in the step S102, the length L of the planta of the foot 39 supported on the adapter 26 is found. For this purpose, the distance from the heel to the tips of the toes is optically measured by the first measuring device 150. The thickness of the adapter is taken into account in calculating the length L of the planta.

In the step S103, the height H of the instep is determined optically by the second measuring device 152. In this determination, the thickness of the adapter is taken into account as described hereinabove. Either S102 or S103 may be performed first, or both these steps may be performed simultaneously.

Next, the measuring position computing unit 156 computes the X coordinate in the step S104, and computes the Y coordinate in the step S105, based on the length L of the planta and height H of the instep found as described above. According to this embodiment, as an example, the measured position of the X coordinate is calculated based on the computational equation X=aL+b. Herein, a and b are predetermined coefficients determined according to the size of the component parts of the apparatus. Likewise, the measuring position computing unit 156 computes the Y coordinate based on the computational equation Y=cH+d. Herein, c and d are predetermined coefficients determined according to the size of the component parts of the apparatus.

Figure 24:
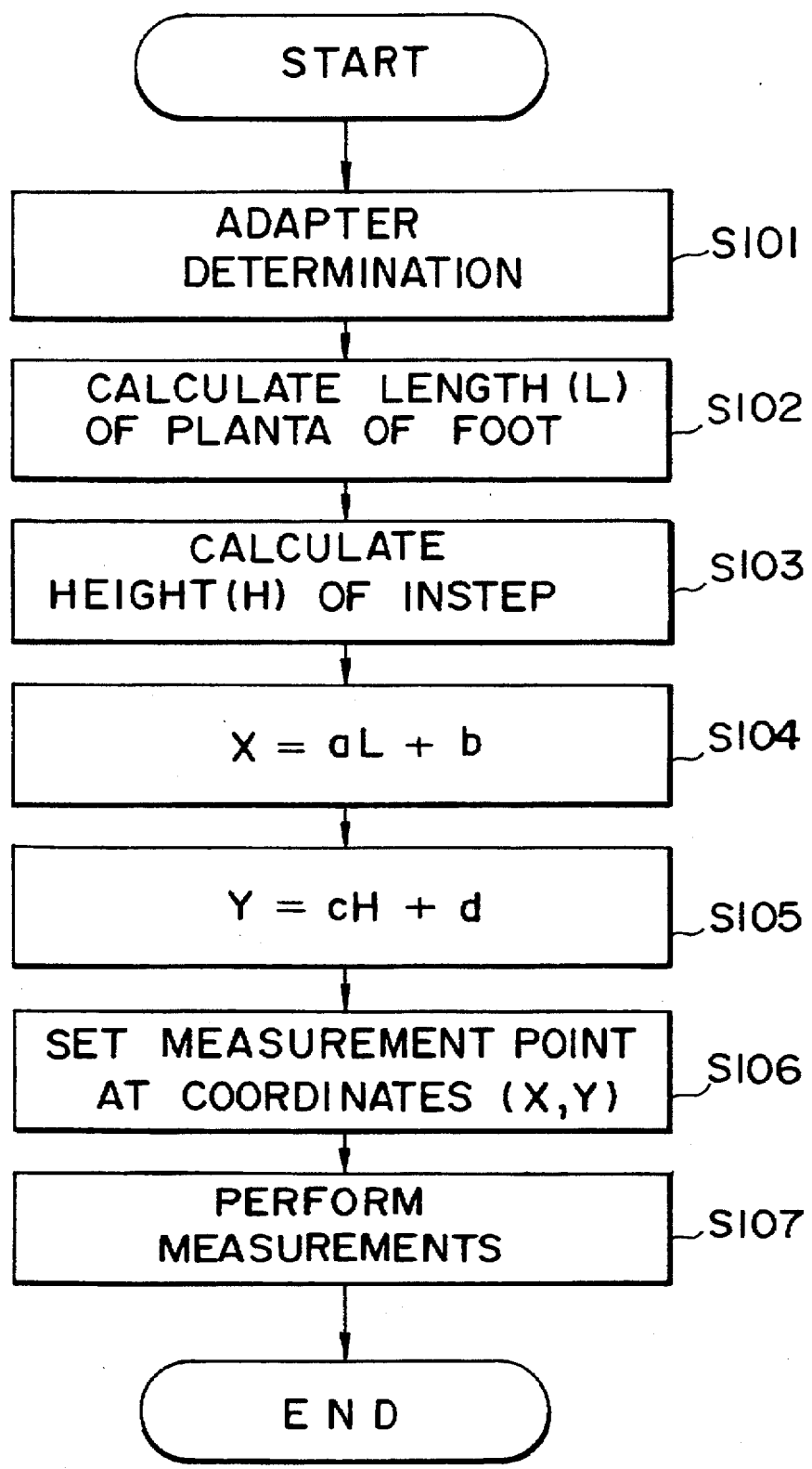
FIG. 24 is a flowchart showing an operation of a measuring unit.

In the example shown in FIG. 24, X and Y are determined based on linear equations, however instead of using these equations, other suitable equations may be chosen based on the geometrical relationships of the component parts of the apparatus.

In the step S106, the coordinates (X, Y) showing a measuring position determined as described hereinabove are output to the transport mechanism 146, and the pair of transducer assemblies 28, 30 is positioned in the X direction and Y direction so that the ultrasonic beam coincides with these coordinates (X, Y). Subsequently, in a step S107, the pair of transducer assemblies 28, 30 is driven in the direction (z direction) in which they approach each other, and the heel is gripped with a predetermined pressure by the pair of transducer assemblies 28, 30.

According to the aforesaid embodiment, an apparatus for diagnosing bone by ultrasonic waves was described, but this invention may be applied also to an apparatus which diagnoses bone using X rays. Also according to the aforesaid example, the first measuring device 150 and second measuring device 152 both detect the length of the planta or height of the instep optically, however this detection may be performed by a mechanical sensor instead of optically.

Further, it is possible that the above fifth embodiment (means for determining and setting the measuring point) is combined with any of the first–fourth embodiments. If this combination is adopted and suitable measurement conditions (irradiating surface and measuring point) are set according to the size of the body part, a highly precise and reliable bone assessment can be performed.

What is claimed is:

1. A bone assessment apparatus for diagnosing bone by transmitting and receiving ultrasonic waves, comprising:

at least one transducer assembly comprising an ultrasonic transducer and a coupler disposed between said transducer and said bone, a drive mechanism for displacing said at least one transducer assembly so that said coupler comes in contact with a body part having said bone therein to be diagnosed, and an adjustment mechanism for adjusting the contact area of said coupler in contact with the body part by controlling said drive mechanism, wherein:

said adjustment mechanism adjusts the ultrasonic wave aperture by adjusting the contact area of said coupler.

2. A bone assessment apparatus as defined in claim 1, wherein:

said coupler comprises a membrane capable of elastic deformation and a coupling liquid filling the interior of this membrane, and said coupler comprises a dome of which the area in contact with the body part to be measured varies according to the pressure on the body part.

3. A bone assessment apparatus as defined in claim 2, wherein:

the contact area of said coupler varies from a minimum area to a maximum area according to increase of contact pressure of said coupler on said body part, and said maximum area is equal to or greater than the area of the vibrating surface of said ultrasonic transducer.

4. A bone assessment apparatus as defined in claim 1, wherein:

said adjustment mechanism comprises:

a plurality of torque limiters having mutually different limiting values which are arranged parallel to each other, and which interrupt transmission of drive torque when the drive torque which drives the transducer assembly reaches a limiting value, and a limiter selector for selectively activating one of said plurality of torque limiters.

5. A bone assessment apparatus as defined in claim 4, wherein:

said limiter selector comprises a plurality of clutches corresponding to said torque limiters.

6. A bone assessment apparatus as defined in claim 1, further comprising:

a size determining unit for determining the size of the body part to be measured, wherein:

said adjusting mechanism adjusts said contact area according to the size of said body part.

7. A bone assessment apparatus as defined in claim 1, wherein:

said adjustment mechanism comprises:

a pressure detector for detecting a pressure of said coupler on said body part, and a stop controller for stopping said transducer assembly from being driven when said pressure reaches a limiting value selected from among said plurality of limiting values.

8. A bone assessment apparatus as defined in claim 7, wherein:

said pressure detector is a sensor for detecting a pressure of a liquid in said coupler.

9. A bone assessment apparatus for diagnosing bone by transmitting and receiving measuring waves, comprising:

at least one assembly comprising an element for emitting said measuring waves, at least one attachment which can be freely attached to or removed from said at least one assembly, said at least one attachment having an aperture for adjusting said measuring waves, said aperture having a periphery comprising an attenuative material, wherein:

the size of the cross-section of the measuring wave beam can be adjusted by fitting said attachment to said assembly.

10. A bone assessment apparatus for diagnosing bone by transmitting and receiving ultrasonic waves, comprising:

at least one transducer assembly comprising an ultrasonic transducer, and at least one attachment which can be freely attached to or removed from at least one transducer said assembly, said at least one attachment having an aperture said aperture having a periphery comprising an attenuative material for adjusting said ultrasonic waves, wherein:

the size of the cross-section of the ultrasonic waves can be adjusted by fitting said attachment to said assembly.

11. A bone assessment apparatus as defined in claim 10, wherein:

a coupler in said transducer assembly projects from said aperture when said at least one attachment is fitted to said transducer assembly, and the material surrounding said aperture is a material which absorbs ultrasonic waves and is capable of elastic deformation.

12. A bone assessment apparatus as defined in claim 10, further comprising:

a connector for fitting said at least one attachment to said at least one transducer assembly.

13. A bone assessment apparatus as defined in claim 12, wherein:

said attaching portion comprises:

a groove formed in said transducer assembly, and a hook formed in said attachment which engages with said groove.

14. A bone assessment apparatus as defined in claim 10, further comprising:

a sensor for detecting the fitting of said attachment.

15. A bone assessment apparatus as defined in claim 10, further comprising:

a size determining unit for determining the size of a body part.

16. A bone assessment apparatus as defined in claim 15, further comprising:

a controller operably connected to said at least one transducer assembly for determining whether or not the attachment is needed in accordance with the size of the body part.

17. A bone assessment apparatus as defined in claim 10, further comprising:

a memory for storing information concerning whether bone measurements were performed with or without the attachment.

18. A method for diagnosing bone by transmitting and receiving ultrasonic waves comprising:

contacting a transducer assembly having an ultrasonic transducer to a body part including the bone to be diagnosed;

transmitting and receiving ultrasonic waves by said ultrasonic transducer;

adjusting a beam size of said ultrasonic waves to correlate with the size of said body part having the bone to be diagnosed; and assessing said bone based upon a received signal obtained by transmission and reception of said ultrasonic waves.

19. The method according to claim 18, wherein said adjusting includes setting said irradiation area to be smaller than an outer shape of the bone to be diagnosed, thereby excluding bodily areas other than said bone.

* * * * *